US011696911B2

(12) United States Patent
Soong

(10) Patent No.: US 11,696,911 B2
(45) Date of Patent: Jul. 11, 2023

(54) ANTIVIRAL COMPOUNDS AND METHOD FOR TREATING RNA VIRAL INFECTION, PARTICULARLY COVID-19

(71) Applicant: SENHWA BIOSCIENCES, INC., New Taipei (TW)

(72) Inventor: Tai-Sen Soong, Chino, CA (US)

(73) Assignee: SENHWA BIOSCIENCES, INC., New Taipei (TW)

( * ) Notice: Subject to any disclaimer, the term of this patent is extended or adjusted under 35 U.S.C. 154(b) by 93 days.

(21) Appl. No.: 17/205,823

(22) Filed: Mar. 18, 2021

(65) Prior Publication Data
US 2021/0308110 A1 Oct. 7, 2021

Related U.S. Application Data

(60) Provisional application No. 63/001,723, filed on Mar. 30, 2020, provisional application No. 63/053,908, filed on Jul. 20, 2020.

(51) Int. Cl.
| | |
|---|---|
| *A61K 31/4745* | (2006.01) |
| *A61K 31/519* | (2006.01) |
| *A61K 31/4375* | (2006.01) |
| *A61P 31/14* | (2006.01) |
| *A61K 31/437* | (2006.01) |

(52) U.S. Cl.
CPC ........ *A61K 31/4375* (2013.01); *A61K 31/437* (2013.01); *A61K 31/519* (2013.01); *A61P 31/14* (2018.01)

(58) Field of Classification Search
CPC .... A61K 31/4745; A61K 31/519; A61P 31/14
USPC .............................................. 514/292, 259.3
See application file for complete search history.

(56) References Cited

U.S. PATENT DOCUMENTS

| | | |
|---|---|---|
| 9,062,043 B2 | 6/2015 | Chua et al. |
| 2011/0071136 A1 | 3/2011 | Haddach et al. |
| 2012/0208792 A1 | 8/2012 | Chua et al. |

FOREIGN PATENT DOCUMENTS

| | | | |
|---|---|---|---|
| WO | WO 2021/195126 A1 * | 9/2021 | .............. A61P 31/14 |
| WO | WO 2021/247367 A1 * | 12/2021 | .............. A61P 31/14 |

OTHER PUBLICATIONS

Shah, B. et al.: In Silica studies on therapeutic agents for COVID-19: Drug repurposing approach. Life Sci., vol. 252, p. 117652, 2020.*
"SID 311420166" PubChem, Available on Feb. 23, 2016, pp. 1-7.
Bouhaddou et al., "The Global Phosphorylation Landscape of SARSCoV- 2 Infection," CellPress, vol. 182, Aug. 6, 2020, pp. 685-712.
Chan et al., "Simulation of the clinical and pathological manifestatioas of Coronavirus Disease 2019 (COVID-19) to golden Syrian hamster model: implications far disease pathogenesis and transmissibility," Clinical infectious diseases : an official publication of the Infectious Diseases Society of America, vol. 71, No. 9, 2020, pp. 2428-2446.
International Search Report and Written Opinion of the International Searching Authority for International Application No. PCT/US2021/022976, dated Sep. 8, 2021.
Sun et al., "Generation of a Broadly Useful Model for COVID-19 Pathogenesis, Vaccination, and Treatment," CellPress, vol. 182, Aug. 6, 2020, pp. 734-743.
Terracciano et al., "Mapping the SARS-CoV-2-Host Protein-Protein Interactome by Affinity PurificationMass Spectrometry and Proximity-Dependent Biotin Labeling: A Rational and Straightforward Route to Discover Host-Directed Anti-SARS-CoV-2 Therapeutics," International Journal of Molecular Sciences, vol. 532, 2021 (Published on Jan. 7, 2021), pp. 1-38.
Wu et al., "Analysis of therapeutic targets for SARS-CoV-2 and discovery of potential drugs by computational methods," Acta Pharmaceutica Sinica B, vol. 10, No. 5, May 2020, pp. 766-788.
Xu et al., "Adaption of Seasonal H1N1 Influenza Virus to Mice," PLoS ONE, vol. 6, No. 12, 2011 (Published on Dec. 16, 2011), pp. 1-11.

* cited by examiner

*Primary Examiner* — Charanjit Aulakh
(74) *Attorney, Agent, or Firm* — Birch, Stewart, Kolasch & Birch, LLP

(57) ABSTRACT

The present invention provides a compound or a method for treating an RNA viral infection in a human, particularly COVID-19. The compound is a certain tricyclic compound.

6 Claims, 4 Drawing Sheets

ANTIVIRAL COMPOUNDS AND METHOD FOR TREATING RNA VIRAL INFECTION, PARTICULARLY COVID-19

CROSS REFERENCE

This application claims the priority on U.S. Patent Provisional Application No. 63/001,723 filed on Mar. 30, 2020, and U.S. Patent Provisional Application No. 63/053,908 filed on Jul. 20, 2020, the entire contents of which are hereby incorporated by reference.

FIELD OF THE INVENTION

The present invention pertains to antiviral compounds, which is capable of treating RNA-viral infection, particularly treating COVID-19.

BACKGROUND OF THE INVENTION

RNA virus is a virus that has ribonucleic acid (RNA) as its genetic material. Human diseases caused by RNA viruses include infections by RNA viruses in the Coronaviridae, Flaviviridae, Picornaviridae, Caliciviridae, Togaviridae, Arteriviridae, Astroviridae or Hepeviridae families.

Human Coronaviruses, first identified in 1960s, are common viruses that infect most people at some time in their life, generally causing mild to moderate upper respiratory and gastrointestinal tract illnesses, which is also referred to as "Middle East Respiratory Syndrome Coronavirus" (MERS-CoV or MERS) that was first reported in Saudi Arabia in 2012. Severe acute respiratory syndrome-related coronavirus (SARS-CoV) responsible for Severe Acute Respiratory Syndrome (SARS) was first recognized in China in 2002.

Among coronaviruses, new Coronavirus disease 2019 (COVID-19) is a new infectious disease caused by severe acute respiratory syndrome coronavirus 2 (SARS-CoV-2), which was first identified in 2019 in Wuhan, China and has spread globally. According to the announcement of World Health Organization (WHO), there are currently more than 110 million confirmed cases in the world, and more than 2.5 million people have died from the coronavirus COVID-19 outbreak as of Mar. 7, 2021. Supportive care is current standard of care. Although some compounds or molecules were reported to be possible to treat Coronavirdae viral infections, there is no promised therapy to treat COVID-19 in humans.

Accordingly, it is desirable to develop an efficient approach for treating Coronavirdae viral infection, particularly COVID-19.

SUMMARY OF THE INVENTION

Accordingly, the present invention provides methods and compounds for the treatment of RNA viral infection.

In one aspect, the present invention provides a method for treating a ribonucleic acid (RNA) viral infection in a human or an animal, which comprises administering to said human or animal a therapeutically effective amount of a compound of Formula (I):

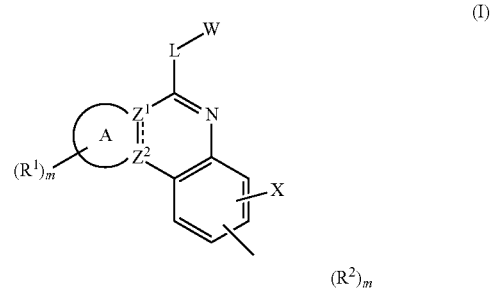

wherein:
A is a saturated or partially saturated optionally substituted 5, 6 or 7 membered ring;
----- represents a single bond or a double bond;
$Z^1$ and $Z^2$ are independently N or C when ----- represents a single bond, provided $Z^1$ and $Z^2$ are not both N; and
$Z^1$ and $Z^2$ are C when ----- represents a double bond;
L is a linker selected from a bond, $NR^3$, O, S, $CR^4R^5$, $CR^4R^5$—$NR^3$, $CR^4R^5$—O—, and $CR^4R^5$—S; each $R^1$, $R^2$, $R^3$, $R^4$ and $R^5$ is independently H, or an optionally substituted member selected from the group consisting of C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, and C6-C12 heteroarylalkyl group, or halo, OR, $NR_2$, NROR, $NRNR_2$, SR, SOR, $SO_2R$, $SO_2NR_2$, $NRSO_2R$, $NRCONR_2$, $NRCSNR_2$, NRC(=NR)$NR^2$, NRCOOR, NRCOR, CN, COOR, $CONR_2$, OOCR, COR, or $NO_2$,
wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and wherein two R on the same atom or on adjacent atoms can be linked to form a 3-8 membered ring, optionally containing one or more N, O or S;
and each R group, and each ring formed by linking two R groups together, is optionally substituted with one or more substituents selected from halo, =O, =N—CN, =N—OR', =NR', OR', $NR'_2$, SR', $SO_2R'$, $SO_2NR'_2$, $NR'SO_2R'$, $NR'CONR'_2$, $NR'CSNR'_2$, NR'C(=NR')$NR'_2$, NR'COOR', NR'COR', CN, COOR', $CONR'_2$, OOCR', COR', and $NO_2$,
wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;
and wherein two R' on the same atom or on adjacent atoms can be linked to form a 3-7 membered ring optionally containing up to three heteroatoms selected from N, O and S;
and $R^1$ can be =O, or two $R^1$ groups on the same atom or on adjacent connected atoms, can optionally be linked together to form a 3-8 membered cycloalkyl or heterocycloalkyl, which is optionally substituted; and $R^4$ and $R^5$, when on the same atom or on adjacent connected atoms, can optionally be linked together to form a 3-8 membered cycloalkyl or heterocycloalkyl, which is optionally substituted;
W is alkyl, heteroalkyl, aryl, heteroaryl, cycloalkyl, heterocyclyl, arylalkyl or heteroarylalkyl, each of which can be optionally substituted;

X is a polar substituent; and each m is independently 0-3; or a pharmaceutically acceptable salt or ester thereof.

In one embodiment of the invention, the compound is the compound of Formula (II):

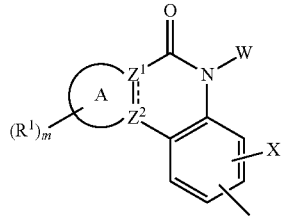

(II)

wherein:
A is a saturated or partially saturated optionally substituted 5, 6 or 7 membered ring;
===== represents a single bond or a double bond;
$Z^1$ and $Z^2$ are independently N or C when ===== represents a single bond, provided $Z^1$ and $Z^2$ are not both N; and
$Z^1$ and $Z^2$ are C when ===== represents a double bond; each of $R^1$ and $R^2$ is independently H, or an optionally substituted member selected from the group consisting of C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, and C6-C12 heteroarylalkyl group, or halo, OR, $NR_2$, NROR, $NRNR_2$, SR, SOR, $SO_2R$, $SO_2NR^2$, $NRSO_2R$, $NRCONR_2$, $NRCSNR_2$, NRC(=NR)$NR^2$, NRCOOR, NRCOR, CN, COOR, $CONR_2$, OOCR, COR, or $NO_2$, wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and wherein two R on the same atom or on adjacent atoms can be linked to form a 3-8 membered ring, optionally containing one or more N, O or S; and
each R group, and each ring formed by linking two R groups together, is optionally substituted with one or more substituents selected from halo, =O, =N—CN, =N—OR', =NR', OR', $NR'_2$, SR', $SO_2R'$, $SO_2NR'_2$, $NR'SO_2R'$, $NR'CONR'_2$, $NR'CSNR'_2$, NR'C(=NR')$NR'_2$, NR'COOR', NR'COR', CN, COOR', $CONR'_2$, OOCR', COR', and $NO_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O; and
wherein two R' on the same atom or on adjacent atoms can be linked to form a 3-7 membered ring optionally containing up to three heteroatoms selected from N, O and S;
and $R^1$ can be =O, or two $R^1$ groups on the same atom or on adjacent connected atoms, can optionally be linked together to form a 3-8 membered cycloalkyl or heterocycloalkyl, which is optionally substituted;
W is alkyl, heteroalkyl, aryl, heteroaryl, cycloalkyl, heterocyclyl, arylalkyl or heteroarylalkyl, each of which can be optionally substituted;
X is a polar substituent; and each m is independently 0-3; or a pharmaceutically acceptable salt or ester thereof.

In some embodiments of Formula (I), the compound has the structure of Formula (I-A) or (I-B):

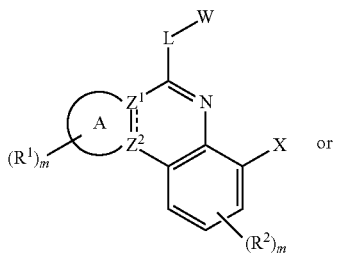

(I-A)

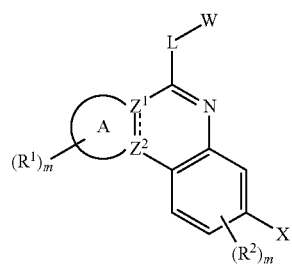

(I-B)

or a pharmaceutically acceptable salt or ester thereof, wherein A, $Z^1$, $Z^2$, L, W, X, $R^1$, $R^2$ and m are defined as in Formula (I).

In some embodiments of the invention, the compound of Formula (II), the compound has the structure of Formula (II-A) or (II-B) below:

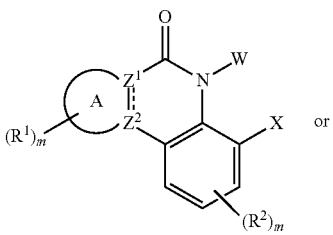

(II-A)

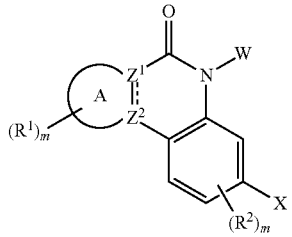

(II-B)

wherein A, $Z^1$, $Z^2$, W, X, $R^1$, $R^2$ and m are defined as in Formula (II).

In the preferred embodiments of the compounds, the compound is one selected from the group consisting of the following compounds:

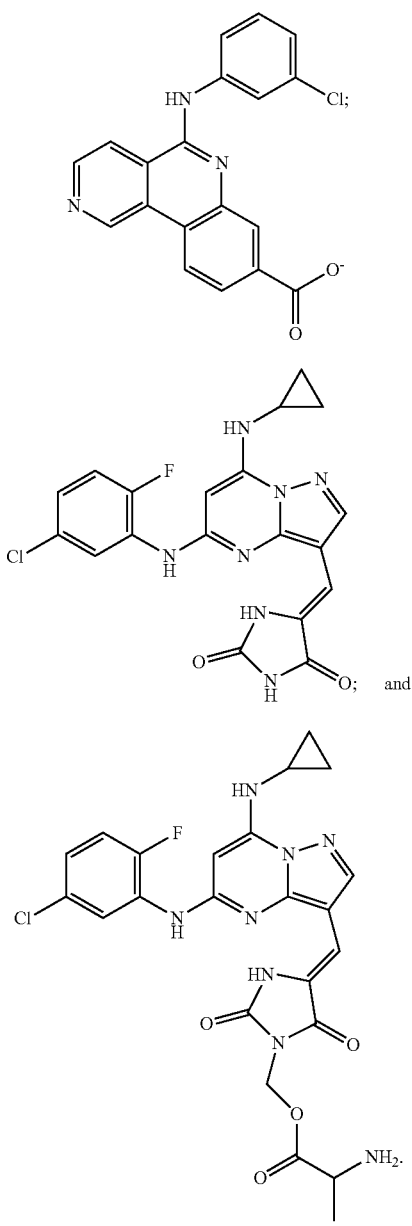

Compound A

Compound B

Compound C

In other aspects, the invention provides an anti-RNA viral pharmaceutical composition in a human or an animal, comprising the compounds as mentioned above.

In the invention, the pharmaceutical composition of the invention comprises a compound described herein and at least one pharmaceutically acceptable carrier or excipient, or one or more pharmaceutically acceptable carriers and/or excipients.

In one further aspect, the invention provides a use of one or more of these compounds for manufacturing a medicament for treating an RNA viral infection, particularly COVID-19.

In one embodiment of the invention, the virus is SARS-CoV-2.

In another embodiment of the invention, the virus is SARS.

In one particular embodiment of the invention, the virus infection is COVID-19 caused by SARS-CoV-2.

Also provided are the compositions comprising the above described molecules in combination with other agents, and methods for using such molecules in combination with one or more of other anti-virus agents.

It is to be understood that both the foregoing general description and the following detailed description are exemplary and explanatory only and are not restrictive of the invention.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiment which is presently preferred. It should be understood, however, that the invention is not limited to this embodiment.

DETAILED DESCRIPTION OF THE INVENTION

Figure 1:
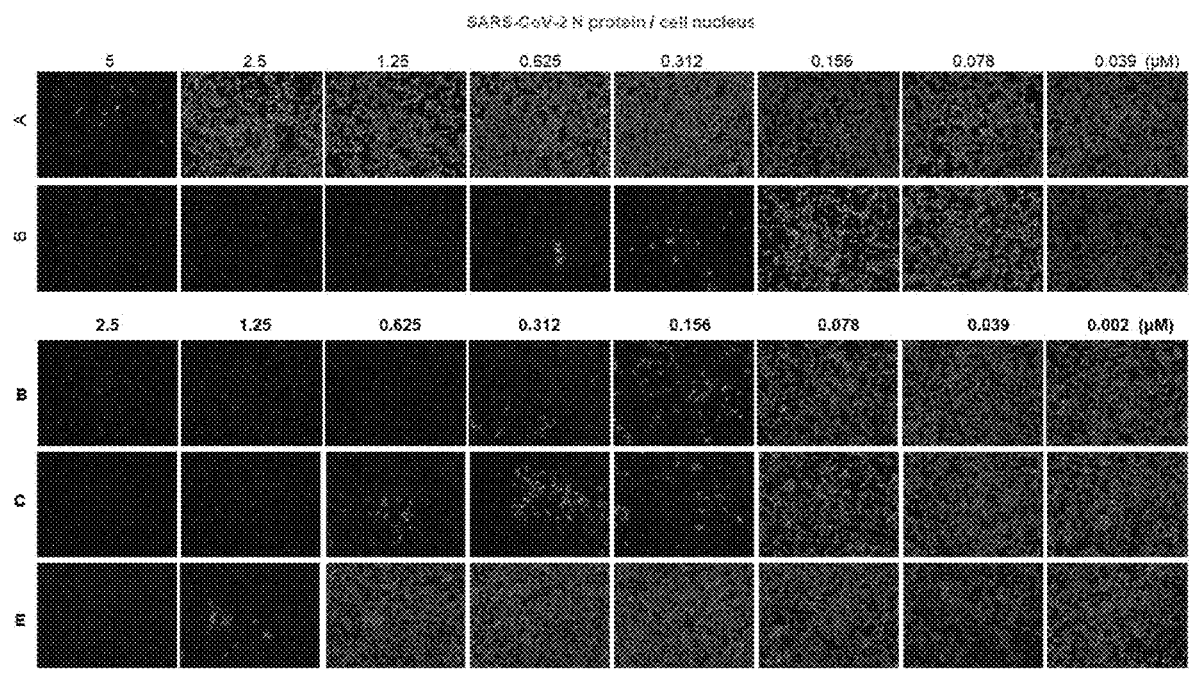
FIG. 1 shows that Vero E6 cells with different concentrations of the Compounds A, B, C, and E were prepared for overnight, and then the cells were infected with SARS-CoV-2 (MOI=0.01) for 2 days. The viral infection was quantified by SARS-CoV-2 N protein expression. SARS-CoV-2 N protein expression and cytotoxicity of the compound was determined by CCK-8 assay.

Unless defined otherwise, all technical and scientific terms used herein have the same meaning as commonly understood by a person skilled in the art to which this invention belongs.

These and other embodiments of the invention are described in the description that follows.

Modes of Carrying Out the Invention

For convenience, and without regard to standard nomenclature, when the position of groups on the bicyclic core portion of Formula (I) and Formula (II) need to be described, the ring positions will be identified by number using the following numbering scheme:

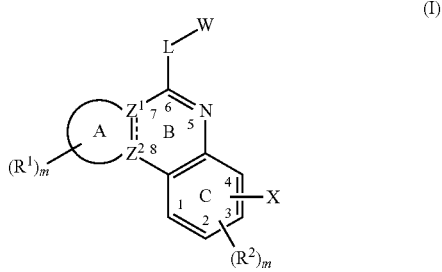

(I)

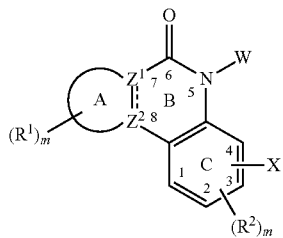

(II)

In this scheme, positions 1-4 are in the lower (phenyl) ring, and positions 5 (Nitrogen) through 8 are in the second ring. So, for example, the position of the polar substituent X on the phenyl ring may be described as position 4 if that group is attached to the unsubstituted carbon adjacent to the phenyl ring carbon attached to N in the second ring. Also for convenience, the phenyl ring is labeled as the C-ring in this structure and throughout the application, while the second ring containing N is referred to as the B-ring. The same relative numbering scheme will be used for other compounds that share the B and C ring bicyclic structure, while the additional ring containing $Z^1$—$Z^2$ fused to this bicyclic group will be referred to as the A-ring herein.

The term "optionally substituted" as used herein refers to the particular group or groups having no non-hydrogen substituents, or the group or groups having one or more non-hydrogen substituents. If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced according to the number of available valences.

The compounds of the invention often have ionizable groups so as to be capable of preparation as salts. In that case, wherever reference is made to the compound, it is understood in the art that a pharmaceutically acceptable salt may also be used. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases are well-known in the art, such as hydrochloric, sulphuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art. In some cases, the compounds may contain both an acidic and a basic functional group, in which case they may have two ionized groups and yet have no net charge.

In some cases, the compounds of the invention contain one or more chiral centers. The invention includes each of the isolated stereoisomeric forms as well as mixtures of stereoisomers in varying degrees of chiral purity, including racemic mixtures. It also encompasses the various diastereomers and tautomers that can be formed. The compounds of the invention may also exist in more than one tautomeric form; the depiction herein of one tautomer is for convenience only, and is also understood to encompass other tautomers of the form shown.

As used herein, the terms "alkyl," "alkenyl" and "alkynyl" include straight-chain, branched-chain and cyclic monovalent hydrocarbyl radicals, and combinations of these, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it can be represented as 1-10C or as C1-C10 or C1-10. When heteroatoms (N, O and S typically) are allowed to replace carbon atoms as in heteroalkyl groups, for example, the numbers describing the group, though still written as e.g. C1-C6, represent the sum of the number of carbon atoms in the group plus the number of such heteroatoms that are included as replacements for carbon atoms in the backbone of the ring or chain being described.

Typically, the alkyl, alkenyl and alkynyl substituents of the invention contain 1-10C (alkyl) or 2-10C (alkenyl or alkynyl). Preferably they contain 1-8C (alkyl) or 2-8C (alkenyl or alkynyl). Sometimes they contain 1-4C (alkyl) or 2-4C (alkenyl or alkynyl). A single group can include more than one type of multiple bond, or more than one multiple bond; such groups are included within the definition of the term "alkenyl" when they contain at least one carboncarbon double bond, and are included within the term "alkynyl" when they contain at least one carboncarbon triple bond.

Alkyl, alkenyl and alkynyl groups are often optionally substituted to the extent that such substitution makes sense chemically. Typical substituents include, but are not limited to, halo, =O, =N—CN, =N—OR, =NR, OR, $NR_2$, SR, $SO_2R$, $SO_2NR^2$, $NRSO_2R$, $NRCONR_2$, $NRCSNR_2$, NRC(=NR)$NR_2$, NRCOOR, NRCOR, CN, C CR, COOR, $CONR_2$, OOCR, COR, and $NO_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halo, =O, =N—CN, =N—OR', =NR', OR', $NR'_2$, SR', $SO_2R'$, $SO_2NR'_2$, NR'$SO_2R'$, NR'CONR'$_2$, NR'CSNR'$_2$, NR'C(=NR')NR'$_2$, NR'COOR', NR'COR', CN, C CR', COOR', CONR'$_2$, OOCR', COR', and $NO_2$, wherein each R' is independently H, C1-C8 alkyl, C2-C8 heteroalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group. Where two R or R' are present on the same atom (e.g., $NR_2$), or on adjacent atoms that are bonded together (e.g., —NR—C(O)R), the two R or R' groups can be taken together with the atoms they are connected to form a 5-8 membered ring, which can be substituted with C1-C4 alkyl, C1-C4 acyl, halo, C1-C4 alkoxy, and the like, and can contain an additional heteroatom selected from N, O and S as a ring member.

"Acetylene" substituents are C2-10C alkynyl groups that are optionally substituted, and are of the formula —C C—$R^a$, wherein $R^a$ is H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and each $R^a$ group is optionally substituted with one or more substituents selected from halo, =O, =N—CN, =N—OR', =NR', OR', $NR'_2$, SR', $SO_2R'$, $SO_2NR'_2$, NR'$SO_2R'$, NR'CONR'$_2$, NR'CSNR'$_2$, NR'C(=NR')NR'$_2$, NR'COOR', NR'COR', CN, COOR', CONR'$_2$, OOCR', COR', and NO$_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-C12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O; and wherein two R' can be linked to form a 3-7 membered ring optionally containing up to three heteroatoms selected from N, O and S. In some embodiments, R$^a$ of —C C—R$^a$ is H or Me. Where two R or R' are present on the same atom (e.g., NR$_2$), or on adjacent atoms that are bonded together (e.g., —NR—C(O)R), the two R or R' groups can be taken together with the atoms they are connected to form a 5-8 membered ring, which can be substituted with C1-C4 alkyl, C1-C4 acyl, halo, C1-C4 alkoxy, and the like, and can contain an additional heteroatom selected from N, O and S as a ring member.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain 1-3 O, S or N heteroatoms or combinations thereof within the backbone residue; thus at least one carbon atom of a corresponding alkyl, alkenyl, or alkynyl group is replaced by one of the specified heteroatoms to form a heteroalkyl, heteroalkenyl, or heteroalkynyl group. The typical and preferred sizes for heteroforms of alkyl, alkenyl and alkynyl groups are generally the same as for the corresponding hydrocarbyl groups, and the substituents that may be present on the heteroforms are the same as those described above for the hydrocarbyl groups. For reasons of chemical stability, it is also understood that, unless otherwise specified, such groups do not include more than two contiguous heteroatoms except where an oxo group is present on N or S as in a nitro or sulfonyl group.

While "alkyl" as used herein includes cycloalkyl and cycloalkylalkyl groups, the term "cycloalkyl" may be used herein to describe a carbocyclic non-aromatic group that is connected via a ring carbon atom, and "cycloalkylalkyl" may be used to describe a carbocyclic non-aromatic group that is connected to the molecule through an alkyl linker. Similarly, "heterocyclyl" may be used to describe a non-aromatic cyclic group that contains at least one heteroatom as a ring member and that is connected to the molecule via a ring atom, which may be C or N; and "heterocyclylalkyl" may be used to describe such a group that is connected to another molecule through a linker. The sizes and substituents that are suitable for the cycloalkyl, cycloalkylalkyl, heterocyclyl, and heterocyclylalkyl groups are the same as those described above for alkyl groups. As used herein, these terms also include rings that contain a double bond or two, as long as the ring is not aromatic.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)NR$_2$ as well as —C(=O)-heteroaryl.

Acyl and heteroacyl groups are bonded to any group or molecule to which they are attached through the open valence of the carbonyl carbon atom. Typically, they are C1-C8 acyl groups, which include formyl, acetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

"Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. Preferably the monocyclic heteroaryls contain 5-6 ring members, and the bicyclic heteroaryls contain 8-10 ring members.

Aryl and heteroaryl moieties may be substituted with a variety of substituents including C1-C8 alkyl, C2-C8 alkenyl, C2-C8 alkynyl, C5-C12 aryl, C1-C8 acyl, and heteroforms of these, each of which can itself be further substituted; other substituents for aryl and heteroaryl moieties include halo, OR, NR$_2$, SR, SO$_2$R, SO$_2$NR$_2$, NRSO$_2$R, NRCONR$_2$, NRCSNR$_2$, NRC(=NR)NR$^2$, NRCOOR, NRCOR, CN, C CR, COOR, CONR$_2$, OOCR, COR, and NO$_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C6-C10 aryl, C5-C10 heteroaryl, C7-C12 arylalkyl, or C6-C12 heteroarylalkyl, and each R is optionally substituted as described above for alkyl groups. Where two R or R' are present on the same atom (e.g., NR$_2$), or on adjacent atoms that are bonded together (e.g., —NR—C(O)R), the two R or R' groups can be taken together with the atoms they are connected to form a 5-8 membered ring, which can be substituted with C1-C4 alkyl, C1-C4 acyl, halo, C1-C4 alkoxy, and the like, and can contain an additional heteroatom selected from N, O and S as a ring member.

The substituent groups on an aryl or heteroaryl group may of course be further substituted with the groups described herein as suitable for each type of such substituents or for each component of the substituent. Thus, for example, an arylalkyl substituent may be substituted on the aryl portion with substituents described herein as typical for aryl groups, and it may be further substituted on the alkyl portion with substituents described herein as typical or suitable for alkyl groups.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically, the linker is C1-C8 alkyl or a hetero form thereof. These linkers may also include a carbonyl group, thus making them able to provide substituents as an acyl or heteroacyl moiety.

An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a C1-C4 alkylene that is unsubstituted or is substituted with one or two C1-C4 alkyl groups or heteroalkyl groups, where the alkyl or heteroalkyl groups can optionally cyclize to form a ring such as cyclopropane, dioxolane, or oxacyclopentane. Similarly, a heteroarylalkyl group preferably includes a C5-C6 monocyclic heteroaryl group that is optionally substituted with the groups described above as substituents typical on aryl groups and a C1-C4 alkylene that is unsubstituted or is substituted with one or two C1-C4 alkyl groups or heteroalkyl groups, or it includes an optionally substituted phenyl ring or C5-C6 monocyclic heteroaryl and a C1-C4 heteroalkylene that is unsubstituted or is substituted with one or two C1-C4 alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus, a benzyl group is a C7-arylalkyl group, and phenylethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene" as used herein refers to a divalent hydrocarbyl group; because it is divalent, it can link two other groups together. Typically it refers to —(CH$_2$)$_n$— where n is 1-8 and preferably n is 1-4, though where specified, an alkylene can also be substituted by other groups, and can be of other lengths, and the open valences need not be at opposite ends of a chain. Thus —CH(Me)- and —C(Me)$_2$- may also be referred to as alkylenes, as can a cyclic group such as cyclopropan-1,1-diyl. Where an alkylene group is substituted, the substituents include those typically present on alkyl groups as described herein.

In general, any alkyl, alkenyl, alkynyl, acyl, or aryl or arylalkyl group or any heteroform of one of these groups that is contained in a substituent may itself optionally be substituted by additional substituents. The nature of these substituents is similar to those recited with regard to the primary substituents themselves if the substituents are not otherwise described. Thus, where an embodiment of, for example, R$^7$ is alkyl, this alkyl may optionally be substituted by the remaining substituents listed as embodiments for R$^7$ where this makes chemical sense, and where this does not undermine the size limit provided for the alkyl per se; e.g., alkyl substituted by alkyl or by alkenyl would simply extend the upper limit of carbon atoms for these embodiments, and is not included. However, alkyl substituted by aryl, amino, alkoxy, =O, and the like would be included within the scope of the invention, and the atoms of these substituent groups are not counted in the number used to describe the alkyl, alkenyl, etc. group that is being described. Where no number of substituents is specified, each such alkyl, alkenyl, alkynyl, acyl, or aryl group may be substituted with a number of substituents according to its available valences; in particular, any of these groups may be substituted with fluorine atoms at any or all of its available valences, for example.

"Heteroform" as used herein refers to a derivative of a group such as an alkyl, aryl, or acyl, wherein at least one carbon atom of the designated carbocyclic group has been replaced by a heteroatom selected from N, O and S. Thus, the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. It is understood that no more than two N, O or S atoms are ordinarily connected sequentially, except where an oxo group is attached to N or S to form a nitro or sulfonyl group.

"Halo", as used herein includes fluoro, chloro, bromo and iodo. Fluoro and chloro are often preferred.

"Amino" as used herein refers to NH$_2$, but where an amino is described as "substituted" or "optionally substituted", the term includes NR'R" wherein each R' and R" is independently H, or is an alkyl, alkenyl, alkynyl, acyl, aryl, or arylalkyl group or a heteroform of one of these groups, and each of the alkyl, alkenyl, alkynyl, acyl, aryl, or arylalkyl groups or heteroforms of one of these groups is optionally substituted with the substituents described herein as suitable for the corresponding group. The term also includes forms wherein R' and R" are linked together to form a 3-8 membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

As used herein, the term "carbocycle" refers to a cyclic compound containing only carbon atoms in the ring, whereas a "heterocycle" refers to a cyclic compound comprising a heteroatom. The carbocyclic and heterocyclic structures encompass compounds having monocyclic, bicyclic or multiple ring systems. As used herein, these terms also include rings that contain a double bond or two, as long as the ring is not aromatic.

As used herein, the term "heteroatom" refers to any atom that is not carbon or hydrogen, such as nitrogen, oxygen or sulfur.

Illustrative examples of heterocycles include but are not limited to tetrahydrofuran, 1,3-dioxolane, 2,3-dihydrofuran, pyran, tetrahydropyran, benzofuran, isobenzofuran, 1,3dihydro-isobenzofuran, isoxazole, 4,5-dihydroisoxazole, piperidine, pyrrolidine, pyrrolidin-2one, pyrrole, pyridine, pyrimidine, octahydro-pyrrolo[3,4 b]pyridine, piperazine, pyrazine, morpholine, thiomorpholine, imidazole, imidazolidine 2,4-dione, 1,3-dihydrobenzimidazol-2one, indole, thiazole, benzothiazole, thiadiazole, thiophene, tetrahydro thiophene 1,1-dioxide, diazepine, triazole, guanidine, diazabicyclo[2.2.1]heptane, 2,5-diazabicyclo[2.2.1]heptane, 2,3,4,4a,9,9a-hexahydro-1H-carboline, oxirane, oxetane, tetrahydropyran, dioxane, lactones, aziridine, azetidine, piperidine, lactams, and may also encompass heteroaryls. Other illustrative examples of heteroaryls include but are not limited to furan, pyrrole, pyridine, pyrimidine, imidazole, benzimidazole and triazole.

As used herein, the term "inorganic substituent" refers to substituents that do not contain carbon or contain carbon bound to elements other than hydrogen (e.g., elemental carbon, carbon monoxide, carbon dioxide, and carbonate). Examples of inorganic substituents include but are not limited to nitro, halogen, azido, cyano, sulfonyls, sulfinyls, sulfonates, phosphates, etc.

The term "polar substituent" as used herein refers to any substituent having an electric dipole, and optionally a dipole moment (e.g., an asymmetrical polar substituent has a dipole moment and a symmetrical polar substituent does not have a dipole moment). Polar substituents include substituents that accept or donate a hydrogen bond, and groups that would carry at least a partial positive or negative charge in aqueous solution at physiological pH levels. In certain embodiments, a polar substituent is one that can accept or donate electrons in a noncovalent hydrogen bond with another chemical moiety.

In certain embodiments, a polar substituent is selected from a carboxy, a carboxy bioisostere or other acid-derived moiety that exists predominately as an anion at a pH of about 7 to 8 or higher. Other polar substituents include, but are not limited to, groups containing an OH or NH, an ether oxygen, an amine nitrogen, an oxidized sulfur or nitrogen, a carbonyl, a nitrile, and a nitrogen-containing or oxygen-containing heterocyclic ring whether aromatic or nonaromatic. In some embodiments, the polar substituent (represented by X) is a carboxylate or a carboxylate bioisostere.

"Carboxylate bioisostere" or "carboxy bioisostere" as used herein refers to a moiety that is expected to be negatively charged to a substantial degree at physiological pH. In certain embodiments, the carboxylate bioisostere is a moiety selected from the group consisting of:

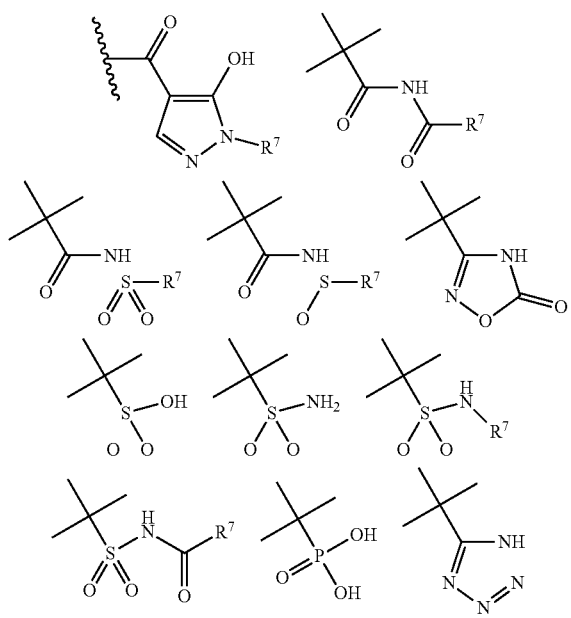

-continued

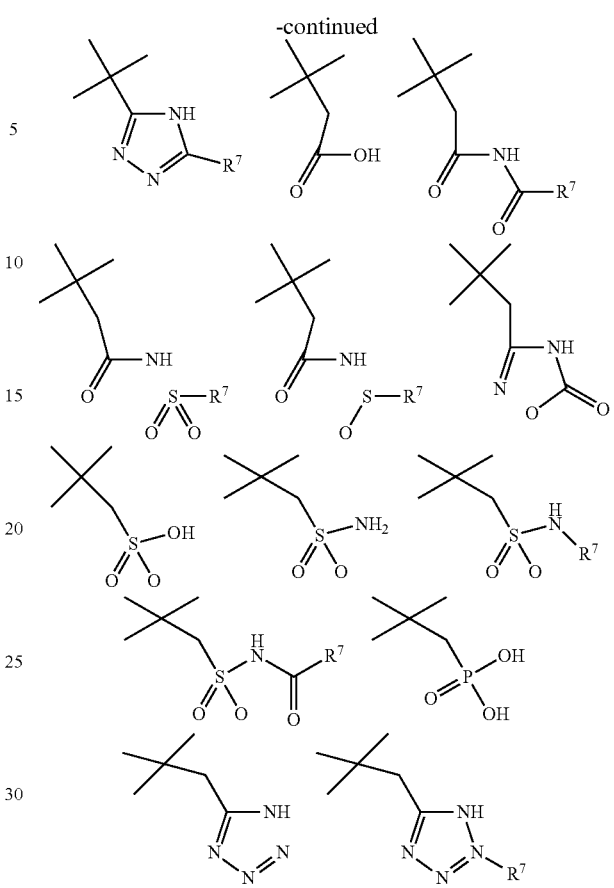

and salts of the foregoing, wherein each $R^7$ is independently H or an optionally substituted member selected from the group consisting of C1-10 alkyl, C2-10 alkenyl, C2-10 heteroalkyl, C3-8 carbocyclic ring, and C3-8 heterocyclic ring optionally fused to an additional optionally substituted carbocyclic or heterocyclic ring; or $R^7$ is a C1-10 alkyl, C2-10 alkenyl, or C2-10 heteroalkyl substituted with an optionally substituted C3-8 carbocyclic ring or C3-8 heterocyclic ring.

In certain embodiments, the polar substituent is selected from the group consisting of carboxylic acid, carboxylic ester, carboxamide, tetrazole, triazole, oxadiazole, oxothiadiazole, thiazole, aminothiazole, hydroxythiazole, and carboxymethanesulfonamide. In some embodiments of the compounds described herein, at least one polar substituent present is a carboxylic acid or a salt, or ester or a bioisostere thereof. In certain embodiments, at least one polar substituent present is a carboxylic acid-containing substituent or a salt, ester or bioisostere thereof. In the latter embodiments, the polar substituent may be a C1-C10 alkyl or C1-C10 alkenyl linked to a carboxylic acid (or salt, ester or bioisostere thereof), for example.

The term "solgroup" or "solubility-enhancing group" as used herein refers to a molecular fragment selected for its ability to enhance physiological solubility of a compound that has otherwise relatively low solubility. Any substituent that can facilitate the dissolution of any particular molecule in water or any biological media can serve as a solubility-enhancing group. Examples of solubilizing groups are, but are not limited to: any substituent containing a group susceptible to being ionized in water at a pH range from 0 to 14; any ionizable group susceptible to form a salt; or any highly polar substituent, with a high dipolar moment and capable of forming strong interaction with molecules of water. Examples of solubilizing groups are, but are not limited to: substituted alkyl amines, substituted alkyl alcohols, alkyl ethers, aryl amines, pyridines, phenols, carboxylic acids, tetrazoles, sulfonamides, amides, sulfonylamides, sulfonic acids, sulfinic acids, phosphates, sulfonylureas.

Suitable groups for this purpose include, for example, groups of the formula -A(CH$_2$)$_{0-4}$-G, where A is absent, O, or NR, where R is H or Me; and G can be a carboxy group, a carboxy bioisostere, hydroxy, phosphonate, sulfonate, or a group of the formula —NR$^y$$_2$ or P(O)(OR$^y$)$_2$, where each R$^y$ is independently H or a C1-C4 alkyl that can be substituted with one or more (typically up to three) of these groups: NH$_2$, OH, NHMe, NMe$_2$, OMe, halo, or =O (carbonyl oxygen); and two Ry in one such group can be linked together to form a 5-7 membered ring, optionally containing an additional heteroatom (N, O or S) as a ring member, and optionally substituted with a C1-C4 alkyl, which can itself be substituted with one or more (typically up to three) of these groups: NH$_2$, OH, NHMe, NMe$_2$, OMe, halo, or =O (carbonyl oxygen).

In some embodiments of the invention, the compound is one of the compounds of Formula (I):

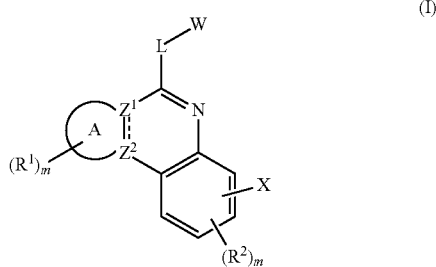

(I)

wherein:
A is a saturated or partially saturated optionally substituted 5, 6 or 7 membered ring; ==== represents a single bond or a double bond;
Z$^1$ and Z$^2$ are independently N or C when ==== represents a single bond, provided Z$^1$ and Z$^2$ are not both N; and Z$^1$ and Z$^2$ are C when ==== represents a double bond;
L is a linker selected from a bond, NR$^3$, O, S, CR$^4$R$^5$, CR$^4$R$^5$—NR$^3$, CR$^4$R$^5$—O—, and CR$^4$R$^5$—S; each R$^1$, R$^2$, R$^3$, R$^4$ and R$^5$ is independently H, or an optionally substituted member selected from the group consisting of C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, and C6-C12 heteroarylalkyl group, or halo, OR, NR$_2$, NROR, NRNR$_2$, SR, SOR, SO$_2$R, SO$_2$NR$^2$, NRSO$_2$R, NRCONR$_2$, NRCSNR$_2$, NRC(=NR)NR$^2$, NRCOOR, NRCOR, CN, COOR, CONR$_2$, OOCR, COR, or NO$_2$, wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and wherein two R on the same atom or on adjacent atoms can be linked to form a 3-8 membered ring, optionally containing one or more N, O or S; and each R group, and each ring formed by linking two R groups together, is optionally substituted with one or more substituents selected from halo, =O, =N—CN, =N—OR', =NR', OR', NR'$_2$, SR', SO$_2$R', SO$_2$NR'$_2$, NR'SO$_2$R', NR'CONR'$_2$, NR'CSNR'$_2$, NR'C(=NR')NR'$_2$, NR'COOR', NR'COR', CN, COOR', CONR'$_2$, OOCR', COR', and NO$_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' on the same atom or on adjacent atoms can be linked to form a 3-7 membered ring optionally containing up to three heteroatoms selected from N, O and S;

and R$^1$ can be =O, or two R$^1$ groups on the same atom or on adjacent connected atoms, can optionally be linked together to form a 3-8 membered cycloalkyl or heterocycloalkyl, which is optionally substituted; and R$^4$ and R$^5$, when on the same atom or on adjacent connected atoms, can optionally be linked together to form a 3-8 membered cycloalkyl or heterocycloalkyl, which is optionally substituted;

W is alkyl, heteroalkyl, aryl, heteroaryl, cycloalkyl, heterocyclyl, arylalkyl or heteroarylalkyl, each of which can be optionally substituted;

X is a polar substituent;

and each m is independently 0-3;

or a pharmaceutically acceptable salt or ester thereof.

In some embodiments, the compound is the compound of Formula (I) having the structure of Formula (I-A) or (I-B), or a pharmaceutically acceptable salt or ester thereof:

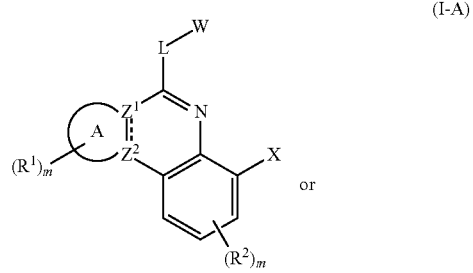

(I-A)

or

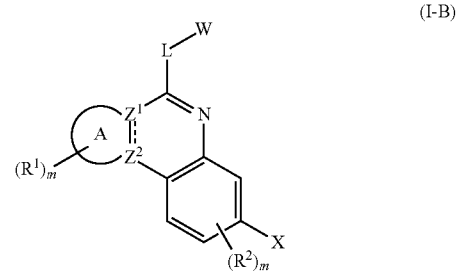

(I-B)

wherein A, Z$^1$, Z$^2$, L, W, X, R$^1$, R$^2$ and m are defined as in Formula (I).

In other embodiments, the compound is the compound of Formula (I) having the structure of Formula (I-C), (I-D) or (I-E), or a pharmaceutically acceptable salt or ester thereof:

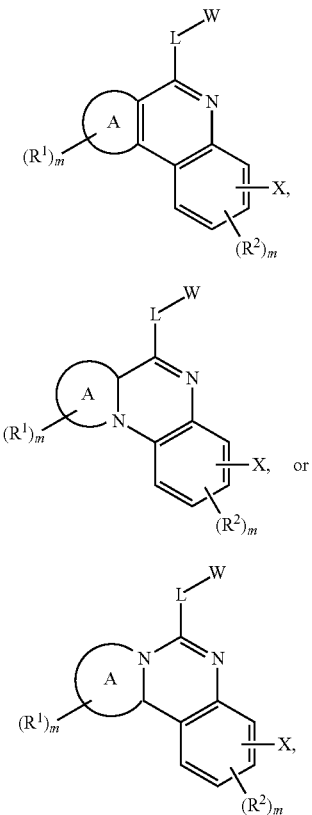

(I-C)

(I-D)

(I-E)

wherein A, L, W, X, R¹, R² and m are defined as in Formula (I).

In another aspect, the invention provides compounds of Formula (II):

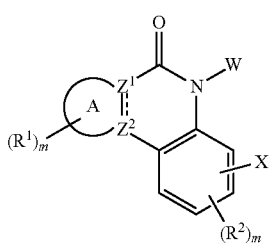

(II)

wherein:
A is a saturated or partially saturated optionally substituted 5, 6 or 7 membered ring;
===== represents a single bond or a double bond;
$Z^1$ and $Z^2$ are independently N or C when ===== represents a single bond, provided $Z^1$ and $Z^2$ are not both N; and $Z^1$ and $Z^2$ are C when ===== represents a double bond;
each of R¹ and R² is independently H, or an optionally substituted member selected from the group consisting of C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, and C6-C12 heteroarylalkyl group, or halo, OR, $NR_2$, NROR, $NRNR_2$, SR, SOR, $SO_2R$, $SO_2NR_2$, $NRSO_2R$, $NRCONR_2$, $NRCSNR_2$, $NRC(=NR)NR_2$, NRCOOR, NRCOR, CN, COOR, $CONR_2$, OOCR, COR, or $NO_2$, wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and wherein two R on the same atom or on adjacent atoms can be linked to form a 3-8 membered ring, optionally containing one or more N, O or S;

and each R group, and each ring formed by linking two R groups together, is optionally substituted with one or more substituents selected from halo, =O, =N—CN, =N—OR', =NR', OR', $NR'_2$, SR', $SO_2R'$, $SO_2NR'_2$, $NR'SO_2R'$, $NR'CONR'_2$, $NR'CSNR'_2$, $NR'C(=NR')NR'_2$, NR'COOR', NR'COR', CN, COOR', $CONR'_2$, OOCR', COR', and $NO_2$,
wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' on the same atom or on adjacent atoms can be linked to form a 3-7 membered ring optionally containing up to three heteroatoms selected from N, O and S;

and R¹ can be =O, or two R¹ groups on the same atom or on adjacent connected atoms, can optionally be linked together to form a 3-8 membered cycloalkyl or heterocycloalkyl, which is optionally substituted;

W is alkyl, heteroalkyl, aryl, heteroaryl, cycloalkyl, heterocyclyl, arylalkyl or heteroarylalkyl, each of which can be optionally substituted;

X is a polar substituent;

and each m is independently 0-3;

or a pharmaceutically acceptable salt or ester thereof.

In some embodiments, the compound of Formula II has the structure of Formula II-A or II-B:

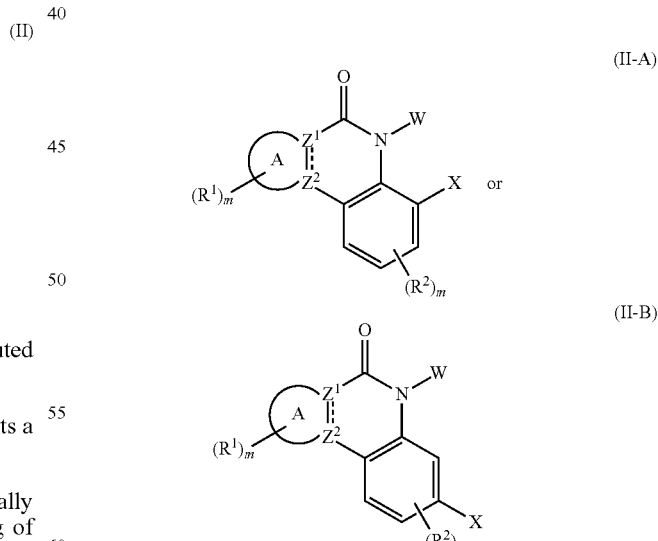

or a pharmaceutically acceptable salt or ester thereof, wherein A, $Z^1$, $Z^2$, W, X, R¹, R² and m are defined as in Formula (II).

In other embodiments, the compound of Formula (II) has the structure of Formula (II-C), (II-D) or (II-E):

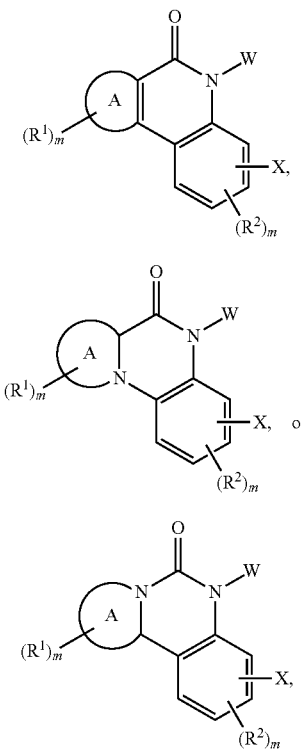

(II-C)

(II-D)

(II-E)

or a pharmaceutically acceptable salt or ester thereof, wherein A, W, X, R$^1$, R$^2$ and m are defined as in Formula (II).

It is understood that as described herein, compounds and embodiments of Formula (I) can include the compounds of Formulae (I-A), (I-B), (I-C), (I-D) and (I-E), and compounds and embodiments of Formula II include compounds of Formulae (II-A), (II-B), (II-C), (II-D) and (II-E).

In compounds of Formulae (I) and (II), A is a saturated or partially saturated optionally substituted 5-, 6- or 7-membered ring. The A-ring may be carbocyclic or heterocyclic ring that is saturated or partially saturated, and may be substituted by groups R$^1$ to the extent such groups make chemical sense.

In some embodiments of Formulae (I) and (II), Z$^1$ and Z$^2$ are independently N or C and $=\!=\!=$ represents a single bond, provided both of Z$^1$ and Z$^2$ are not N.

In other embodiments of Formulae (I) and (II), Z$^1$ and Z$^2$ are C and $=\!=\!=$ represents a double bond.

In compounds of Formulae (I) and (II), the A-ring comprises an optionally substituted 5-7 membered ring. In some embodiments, the A-ring is an optionally substituted 5-7 membered ring carbocyclic ring. For example, ring A is an optionally substituted cyclopentane, cyclopentene, cyclohexane, cyclohexene, cycloheptane or cycloheptene ring.

In other embodiments, the A-ring comprises an optionally substituted 5-7 membered heterocyclic ring, containing at least one heteroatom selected from N, O, and S. In some such embodiments, one of Z$^1$ and Z$^2$ is N, and there are no additional heteroatoms in the A-ring. In other such embodiments, one of Z$^1$ and Z$^2$ is N, and there is an additional heteroatom selected from O, N and S in the A-ring. In certain embodiments, ring A is an optionally substituted dihydrofuran, tetrahydrofuran, dihydrothiophene, tetrahydrothiophene, dihydropyrrole, pyrrolidine, dihydropyran, tetrahydropyran, pyran, dihydrothiopyran, tetrahydrothiopyran, thiopyran, piperidine, dihydropyridine, tetrahydropyridine, imidazoline, thiazolidine, oxazolidine, dihydrothiazole, dihydrooxazole, morpholine, thiomorpholine, piperazine, dihydropyrimidine, azepine, dihydroazepine, tetrahydroazepine, hexahydroazepine ring, homomorpholine, homothiomorpholine, dizaepine, dihydrodiazepine, tetrahydrodiazepine, hexahydrodiazepine ring, oxepane, or thiooxepane ring.

Sometimes, the A-ring containing is selected from the group consisting of:

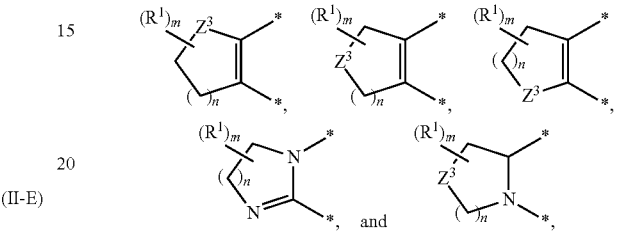

wherein Z$^3$ is CR$^1{}_2$, NR$^1$, S(=O)$_p$, or O; n is 1-3; and p is 0-2.

In compounds of Formula (I), L is a linker selected from a bond, NR$^3$, O, S, CR$^4$R$^5$, CR$^4$R$^5$—NR$^3$, CR$^4$R$^5$—O—, and CR$^4$R$^5$—S. Where L is a two-atom linker, it can be attached to the ring system through either end, i.e., either the carbon atom or the heteroatom of CR$^3$R$^4$—NR$^5$, CR$^3$R$^4$—O—, and CR$^3$R$^4$—S can be attached to the ring, and the other atom is attached to L. In some embodiments, L is a bond, or a 1-2 atom linker, including —N(R$^3$)—, —O—, —S—, —CH$_2$—N(R$^3$), —N(R$^3$)—CH$_2$—, —O—CH$_2$—, —CH$_2$—O—, —CH$_2$—S—, —S—CH$_2$—, —CMe$_2$N(R$^3$)—, —CMe$_2$-O—, —N(R$^3$)—CMe$_2$, —O—CMe$_2$-, and the like. In certain embodiments, L is selected from a bond, NH, NMe, and CH$_2$—N(R$^3$)— or —N(R$^3$)—CH$_2$—, where R$^3$ is H or Me.

In some embodiments of Formula (I), L is NH or NMe. In other embodiments, L can be NAc, where Ac represents a C1-C10 acyl group, i.e., L is a group of the formula N—C(=O)—R$^z$, where R$^z$ is H or a C1-C9 optionally substituted alkyl group. These can serve as pro-drugs for compounds where L is NH. In still other embodiments, L is a bond; in these embodiments, W is often an aryl or heteroaryl, which is optionally substituted.

In some embodiments of Formulae (I) and (II), W is selected from optionally substituted aryl, optionally substituted heteroaryl, optionally substituted cycloalkyl, optionally substituted heterocyclyl, optionally substituted arylalkyl, and optionally substituted heteroarylalkyl. For example, W can be an optionally substituted phenyl, pyridyl, pyrimidinyl, or pyrazinyl group; or a napthyl, indole; benzofuran, benzopyrazole, benzothiazole, quinoline, isoquinoline, quinazoline or quinoxaline group. Suitable substituents for these groups include, but are not limited to, halo, C1-C4 alkyl, C2-C4alkenyl or alkynyl, CN, OMe, COOMe, COOEt, CONH$_2$, CF$_3$, and the like, and typically the aryl group is substituted by up to 2 of these groups. In certain preferred embodiments, when W is aryl or heteroaryl, it is unsubstituted, or it is substituted by 1 or 2 substituents.

In some embodiments of Formulae (I) and (II), W is optionally substituted phenyl, optionally substituted heterocyclyl, or C1-C4 alkyl substituted with at least one member selected from the group consisting of optionally substituted phenyl, optionally substituted heteroalkyl, optionally substituted heteroaryl, halo, hydroxy and —NR"$_2$, where each R" is independently H or optionally substituted C1-C6 alkyl; and two R" taken together with the N to which they are attached can be linked together to form an optionally substituted 3-8 membered ring, which can contain another heteroatom selected from N, O and S as a ring member, and can be saturated, unsaturated or aromatic.

In some such compounds, W comprises at least one group of the formula —(CH$_2$)$_p$—NR$^x$$_2$, where p is 1-4, R$^x$ is independently at each occurrence H or optionally substituted alkyl; and two R$^x$ taken together with the N to which they are attached can be linked together to form an optionally substituted 3-8 membered ring, which can contain another heteroatom selected from N, O and S as a ring member, and can be saturated, unsaturated or aromatic.

In some embodiments, W can be aryl (e.g., phenyl), heterocyclic (e.g., pyrrolidine, piperidine, morpholine, piperazine, thiomorpholine), or heteroaryl (e.g., pyrrole, pyridine, pyrazine, pyrimidine, furan, thiophene, thiazole, isothiazole, thiadiazole, oxazole, isoxazole, imidazole, pyrazole, triazole, triazine, tetrazole and the like, each of which can be substituted. In some such embodiments, it is selected from phenyl, pyrrolidine, piperidine, piperazine, morpholine, and the like. In other embodiments, W can be arylalkyl or heteroarylalkyl, where the aryl and heteroaryl moieties of these groups are selected from the groups described above, attached to a C1-6 and preferably a C1-4 alkylene or heteroalkylene moiety. W can be substituted by a variety of substituents. In certain embodiments, W is an aryl ring substituted by a group of the formula —(CH$_2$)$_{0-4}$—NR$^x$$_2$, where each R$^x$ can be H or C1-C4 alkyl, and can be substituted, and where two Rx can optionally cyclize into a ring. In some embodiments, this group is of the formula —(CH$_2$)$_{0-4}$-Az, where Az represents an azacyclic group such as pyrrolidine, piperidine, morpholine, piperazine, thiomorpholine, pyrrole, and the like. In some embodiments, this group is —(CH$_2$)$_{1-3}$-Az, where Az is 4-morpholinyl, 1-piperazinyl, 1pyrrolidinyl, or 1-piperidinyl; —CH$_2$—CH$_2$-Az, where Az is 4-morpholinyl is one exemplary substituent for W, when W is substituted.

In some embodiments of Formulae (I) and (II), X is selected from the group consisting of COOR$^9$, C(O)NR$^9$—OR$^9$, triazole, tetrazole (preferably linked to the phenyl ring via the carbon atom of the tetrazole ring), CN, imidazole, carboxylate, a carboxylate bioisostere,

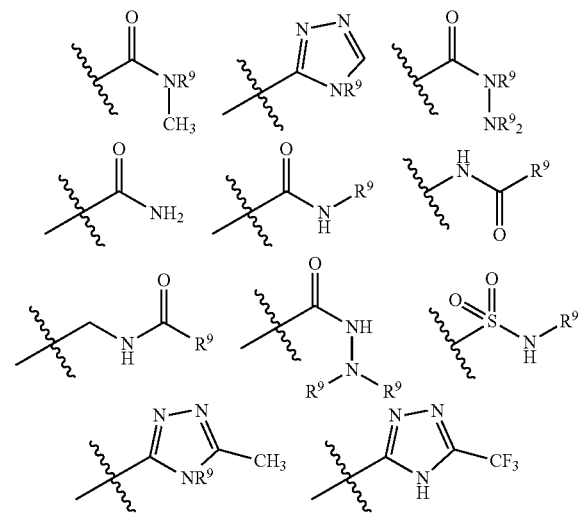

-continued

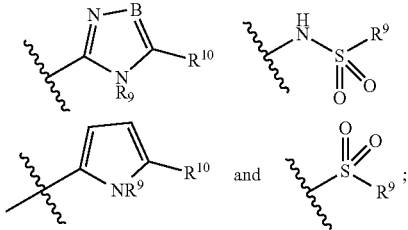

wherein each R$^9$ is independently H or an optionally substituted member selected from the group consisting of alkyl, cycloalkyl, heterocyclyl, aryl, heteroaryl, arylalkyl, cycloalkylalkyl, heterocycloalkylalkyl, and heteroarylalkyl, and two R$^9$ on the same or adjacent atoms can optionally be linked together to form an optionally substituted ring that can also contain an additional heteroatom selected from N, O and S as a ring member;

R$^{10}$ is halo, CF$_3$, CN, SR, OR, NR$_2$, or R, where each R is independently H or optionally substituted C1-C6 alkyl, and two R on the same or adjacent atoms can optionally be linked together to form an optionally substituted ring that can also contain an additional heteroatom selected from N, O and S as a ring member; and B is N or CR$^{10}$.

In compounds of Formulae (I) and (II), at least one polar substituent X may be at any position on the phenyl ring (C-ring), and the ring may include one, two, three or four polar substituents. In compounds of Formulae (I-A), (I-B), (II-A), and (II-B), the molecule contains at least one polar group, X, at the position indicated by the structure, and the ring may include one, two, three or four polar substituents. In certain embodiments, there is one polar group, X, and each R$^2$ is H, or up to two R$^2$ are substituents described herein other than H, such as, for example only, Me, Et, halo (especially F or Cl), MeO, CF$_3$, CONH$_2$, or CN. A polar group can be at any position on the phenyl ring. In some embodiments, the phenyl ring is selected from the following options, which are oriented to match the orientation of Formula (I) herein, and depict the position of the polar substituent X:

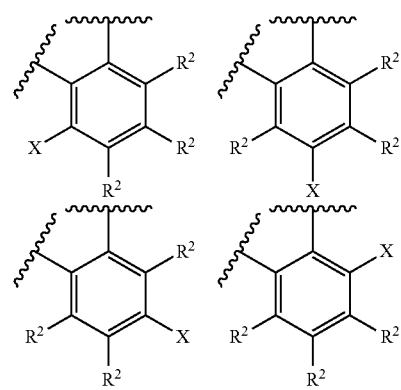

where X is a polar substituent and each R$^2$ is independently is selected from R$^2$ substituents, as defined above with respect to compounds of Formulae (I) and (II).

In some embodiments of the above-described compounds, the polar substituent X is located at position 4 on the phenyl ring. In alternative embodiments, the polar substituent X is located at position 3 on the phenyl ring. In certain embodiments, the polar substituent is a carboxylic acid or a tetrazole, and is at position 3 or 4 on the phenyl ring.

In some embodiments of these compounds, the phenyl ring (i.e., C-ring) is substituted by up to three additional substituents, in addition to the polar substituent X. Suitable substituents for the phenyl are described above. In some embodiments, these substituents are selected from halo, C1-C4 alkyl, C1-C4 haloalkyl, C1-C4 alkoxy, amino, C1-C4 alkylthio, and CN. In some embodiments, there is only one such substituent (i.e., m is 1), or there is no additional substituent besides the polar substituent X, i.e., m is 0.

In some embodiments of Formula (I), -L-W is selected from:

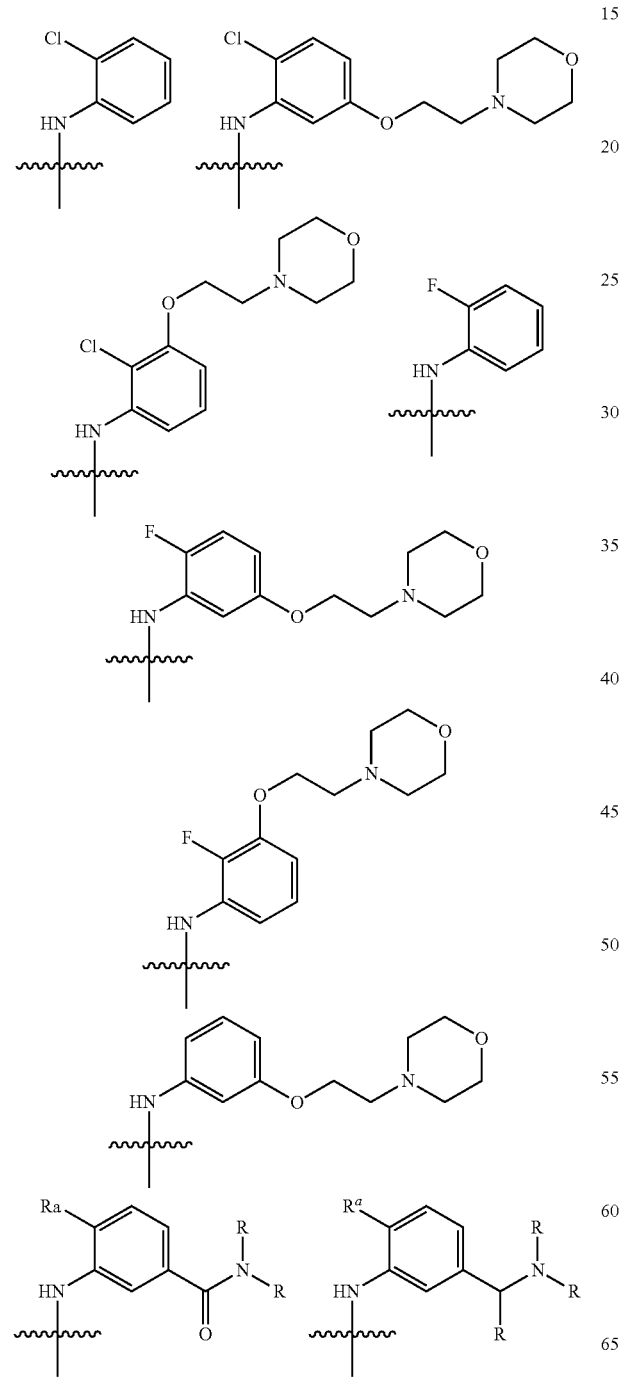
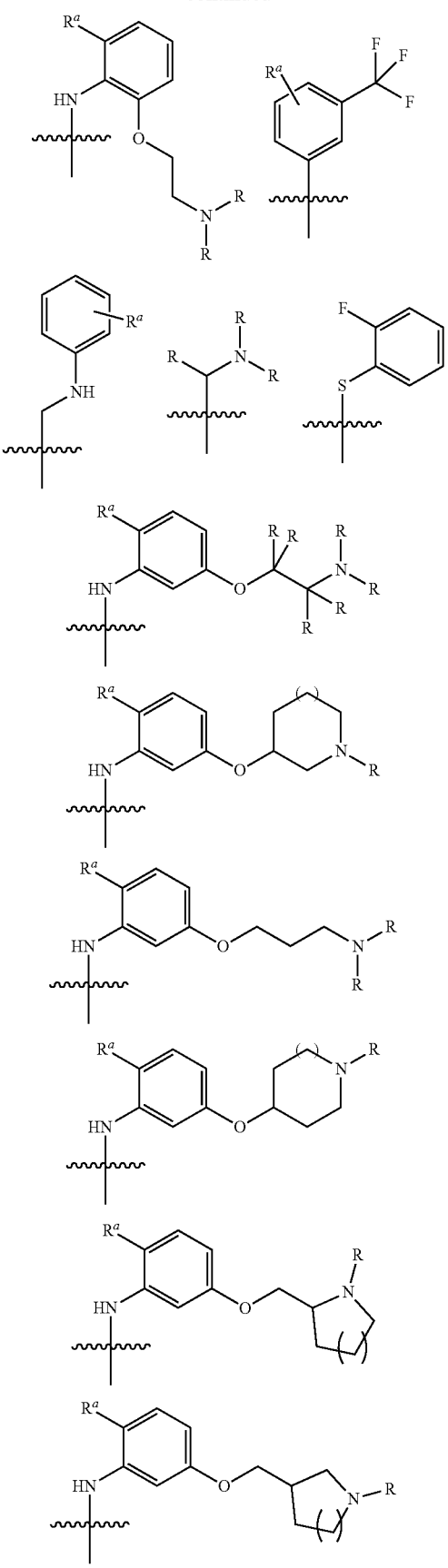

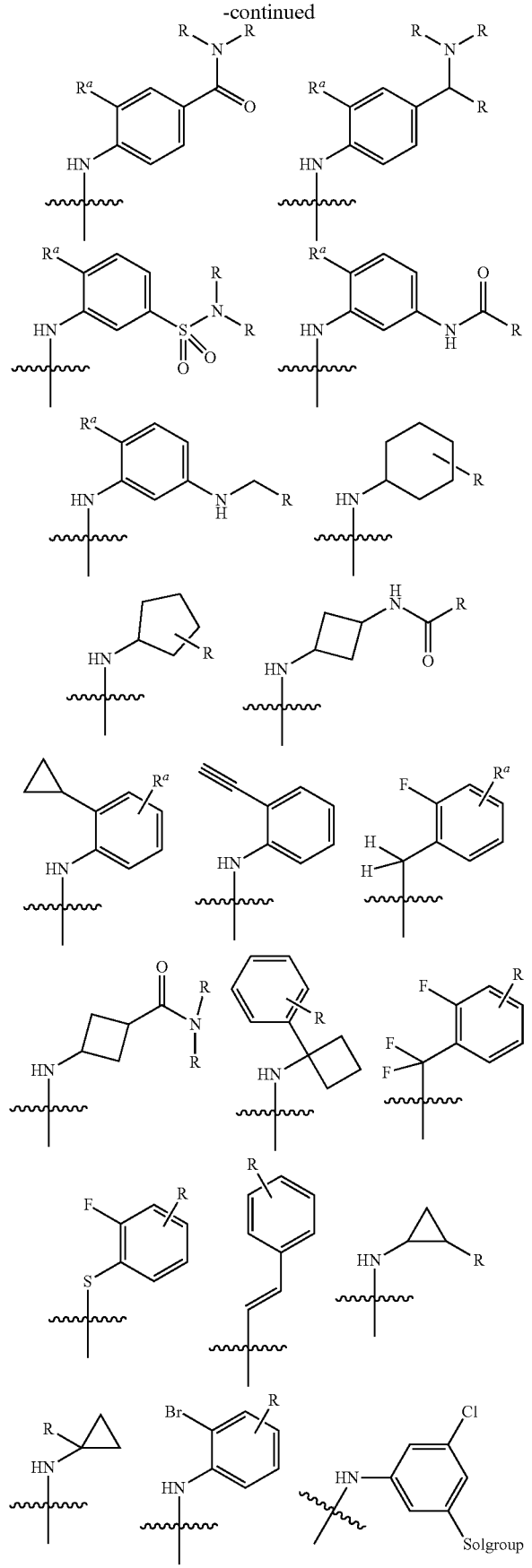
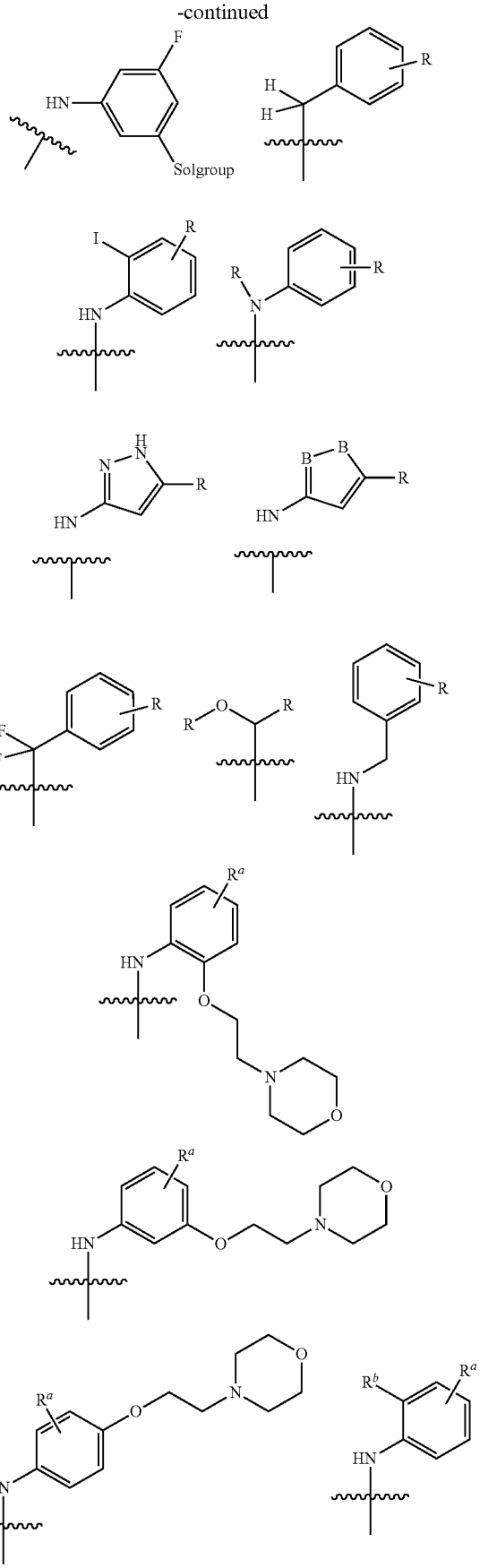

-continued

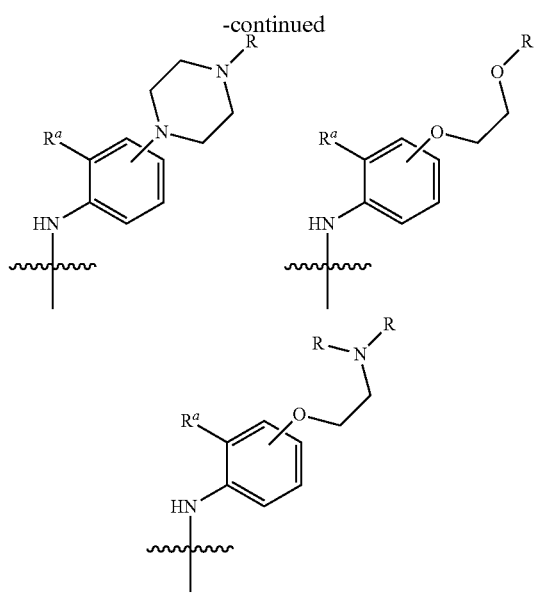

wherein each $R^a$ is independently H, Cl or F;
each $R^b$ is independently Me, F, or Cl;
each R is independently selected from H, halo, C1-C4 alkyl, C1-C4 alkoxy, and C1-C4 haloalkyl, and two R groups on the same or adjacent connected atoms can optionally be linked together to form a 3-8 membered ring;
each B is N or CR;
and each Solgroup is a solubility-enhancing group.

The most preferred compounds are Silmitasertib also known as Compound A (disclosed in U.S. Pat. No. 9,062,043), Compound B (disclosed in U.S. Pat. No. 8,575,177), and Compound C (disclosed in U.S. Pat. No. 8,575,177), or a pharmaceutically acceptable salt or ester thereof:

Compound A

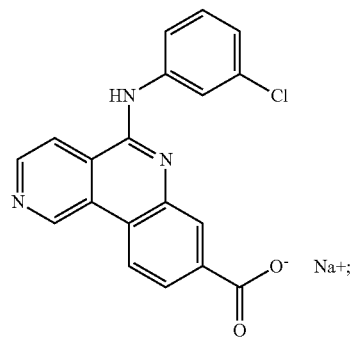

Compound B

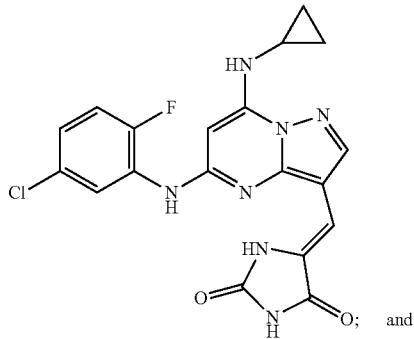
and

-continued

Compound C

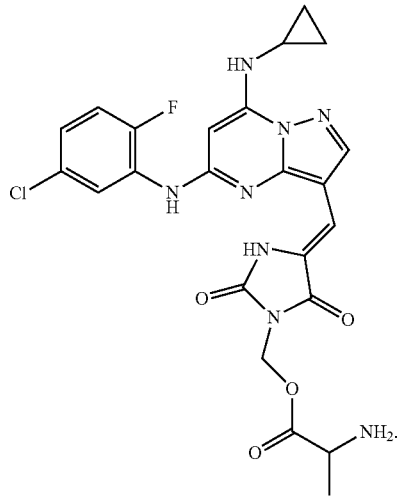

In one aspect, the invention provides a method for treating RNA virus infection in a human, which comprises administering to said human a therapeutically effective amount of one or combination thereof of these compounds.

In another aspect, the invention provides a pharmaceutical composition for treating RNA virus infection. The pharmaceutical compositions can comprise a compound of any of the formulae described herein, admixed with at least one pharmaceutically acceptable excipient or carrier. Frequently, the composition comprises at least two pharmaceutically acceptable excipients or carriers.

In a further aspect, the invention provides a use of one of these compounds for manufacturing a medicament for treating an RNA virus infection in a human or an animal.

In the invention, it is ascertained that some virus infections can be treated using these compounds described herein.

Particularly for RNA viruses, the virus infections are caused by Coronaviridae.

In the invention, the term "Coronaviridae virus" or "Coronavirus" refers to a family of enveloped, positive-sense, single-stranded RNA viruses, which includes but not limited to Middle East respiratory syndrome-related coronavirus (MERS-CoV), severe acute respiratory syndrome-related coronavirus (SARS-CoV), SARS-COV-2 (associated with COVID-19), 229E, NL63, human coronavirus OC43 (HCoV-OC43), and CoV-HKU1. In one particular embodiment of the invention, the compounds of the invention are effective in treating a COVID-19 infection.

The terms "treat" and "treating" as used herein refer to ameliorating, alleviating, lessening, and removing symptoms of a disease or condition caused by a Coronavirus infection. A candidate molecule or compound described herein may be in a therapeutically effective amount in a formulation or medicament, which is an amount that can lead to a biological effect, such as anti-virus effect, or lead to ameliorating, alleviating, lessening, or removing symptoms of a disease or condition, for example.

Formulations and Routes of Administration

Any suitable formulation of a compound described above can be prepared for administration. Any suitable route of administration may be used, including, but not limited to, oral, parenteral, intravenous, intramuscular, transdermal, topical and subcutaneous routes. Depending on the subject to be treated, the mode of administration, and the type of treatment desired—e.g., prevention, prophylaxis, therapy; the compounds are formulated in ways consonant with these parameters. Preparation of suitable formulations for each route of administration are known in the art. A summary of such formulation methods and techniques is found in *Remington's Pharmaceutical Sciences*, latest edition, Mack Publishing Co., Easton, Pa., which is incorporated herein by reference. The formulation of each substance or of the combination of two substances will generally include a diluent as well as, in some cases, adjuvants, buffers, preservatives and the like. The substances to be administered can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised, and can be applied to compounds of the invention. See, for example, U.S. Pat. No. 5,624,677, the methods of which are incorporated herein by reference.

Systemic administration may also include relatively non-invasive methods such as the use of suppositories, transdermal patches, transmucosal delivery and intranasal administration. Oral administration is also suitable for compounds of the invention. Suitable forms include syrups, capsules, tablets, as is understood in the art.

For administration to animal or human subjects, the appropriate dosage of a compound described above often is 0.01-15 mg/kg, and sometimes 0.1-10 mg/kg. Dosage levels are dependent on the nature of the condition, drug efficacy, the condition of the patient, the judgment of the practitioner, and the frequency and mode of administration; however, optimization of such parameters is within the ordinary level of skill in the art.

The amount of each of these materials to be administered will vary with the route of administration, the condition of the subject, other treatments being administered to the subject, and other parameters. The therapeutic agents of the invention may, of course, cause multiple desired effects; and the amount of modulator to be used in combination with the therapeutic agent should be an amount that increases one or more of these desired effects. An amount is "effective to enhance a desired effect of the therapeutic agent", as used herein, if it increases by at least about 25% at least one of the desired effects of the therapeutic agent alone. Preferably, it is an amount that increases a desired effect of the therapeutic agent by at least 50% or by at least 100% (i.e., it doubles the effective activity of the therapeutic agent.) In some embodiments, it is an amount that increases a desired effect of the therapeutic agent by at least 200%.

When a compound or composition of the invention is used in combination with another agent or therapeutic agent, the present invention provides, for example, simultaneous, staggered, or alternating treatment. Thus, the compound of the invention may be administered at the same time as an anti-virus agent or additional therapeutic agent, in the same pharmaceutical composition; the compound of the invention may be administered at the same time as the other agent, in separate pharmaceutical compositions; the compound of the invention may be administered before the other agent, or the other agent may be administered before the compound of the invention, for example, with a time difference of seconds, minutes, hours, days, or weeks.

The compound of the invention and the additional therapeutic agent may be administered in the same dosage form, e.g., both administered as intravenous solutions, or they may be administered in different dosage forms, e.g., one compound may be administered topically and the other orally. A person of ordinary skill in the art would be able to discern which combinations of agents would be useful based on the particular characteristics of the drugs and the cancer involved.

Additional therapeutic agents useful for therapy in combination with the compounds of the invention include the following types of agents and inhibitors:

Compounds of the invention can be prepared using available methods and reagents, based on the ordinary level of skill in the art and methods. The preparation of the compounds as previously described in WO2009061131, U.S. Pat. Nos. 7,956,064, 9,062,043 and 8,575,177.

Experiments on Antiviral Activity
Materials and Methods
Compounds
The compounds below were tested:
Compound A
Compound B
Compound C
Compound E: Remdesivir (Positive Control Compound)
The compounds were dissolved in DMSO as stock solutions.

Experiment 1. SARS-CoV-2 Infection and Immunofluorescent Assay (IFA)

Vero E6 cells were pretreated with the indicated compound at various concentrations for 20 hr at 37° C. and then infected with SARS-CoV-2 (TCDC #4 from Taiwan CDC) at MOI=0.01 for 2 days. The cells were fixed with 10% formalin and permeabilized with 0.5% Triton X-100 in PBS. The cells were stained with a human anti-SARS-CoV-2 N protein monoclonal antibody (provided by Dr. An-Suei Yang in Genomics Research Center, Academia Sinica, Taipei, Taiwan) and goat anti-human IgG-Alexa Fluor 488 (A11013, Invitrogen). Cell nucleus was stained with DAPI (D1306, Invitrogen). The signals were observed and photographed under an immunofluorescent microscope. To quantify viral infection, images were acquired and analyzed using an ImageXpress Micro XLS Widefield High-Content Analysis System (Molecular Devices). For cell viability test, Vero E6 cells were treated with the indicated compound at different dilutions for 1 day at 37° C. The cell viability was determined by Cell Counting Kit-8 (CCK-8). 50% inhibition concentration (IC50) and 50% cytotoxic concentration (CC50) were calculated by Prism software.

Experiment 2. SARS-CoV-2 Plaque Reduction Neutralization Test (PRNT).

Vero E6 cells were pretreated with the indicated compound at various concentrations for 20 hr at 37° C. The cells were infected with SARS-CoV-2 at MOI=0.01 TCID$_{50}$ for 2 days at 37° C. The cells were fixed with 10% formalin and penetrated with 0.5% Triton X-100. The cells were stained with anti-SARS-CoV-2 N protein antibody and anti-human IgG-488 (green). The nuclei were stained with DAPI (blue). The N protein expression was measured using a high-content image analysis system. The IC50 and CC50 were calculated by Prism software.

For cell viability test, the Vero E6 cells were treated with each compound with indicated dilution for 2 day at 37° C. The cell viability was determined by Cell Counting Kit-8 (CCK-8).

Figure 2:
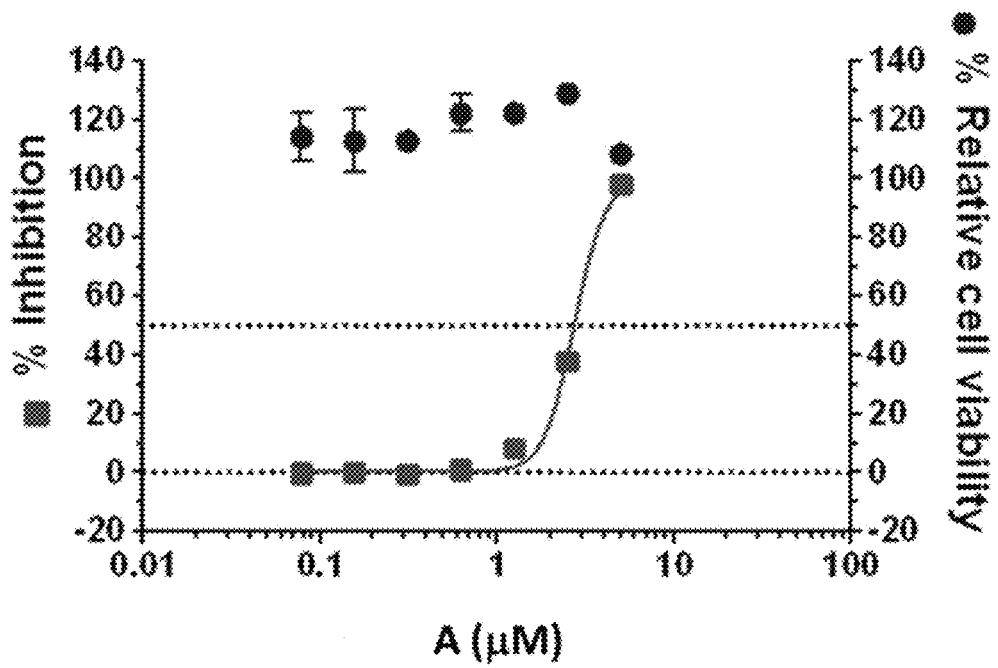
FIG. 2 shows that Compound A provided anti-SARS-CoV-2 activity, with IC50 at 2.743 µM and CC50>5 µM.
Figure 3:
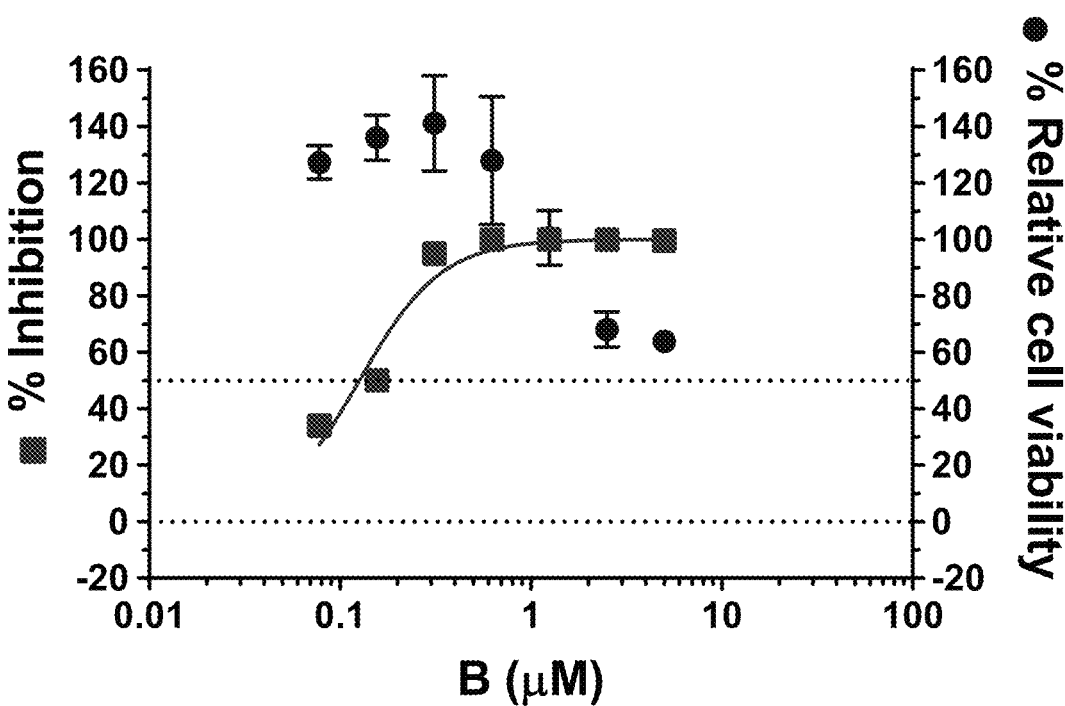
FIG. 3 shows that Compound B provided anti-SARS-CoV-2 activity, with IC50 at 126.3 nM and CC50 at 5.897 µM.
Figure 4:
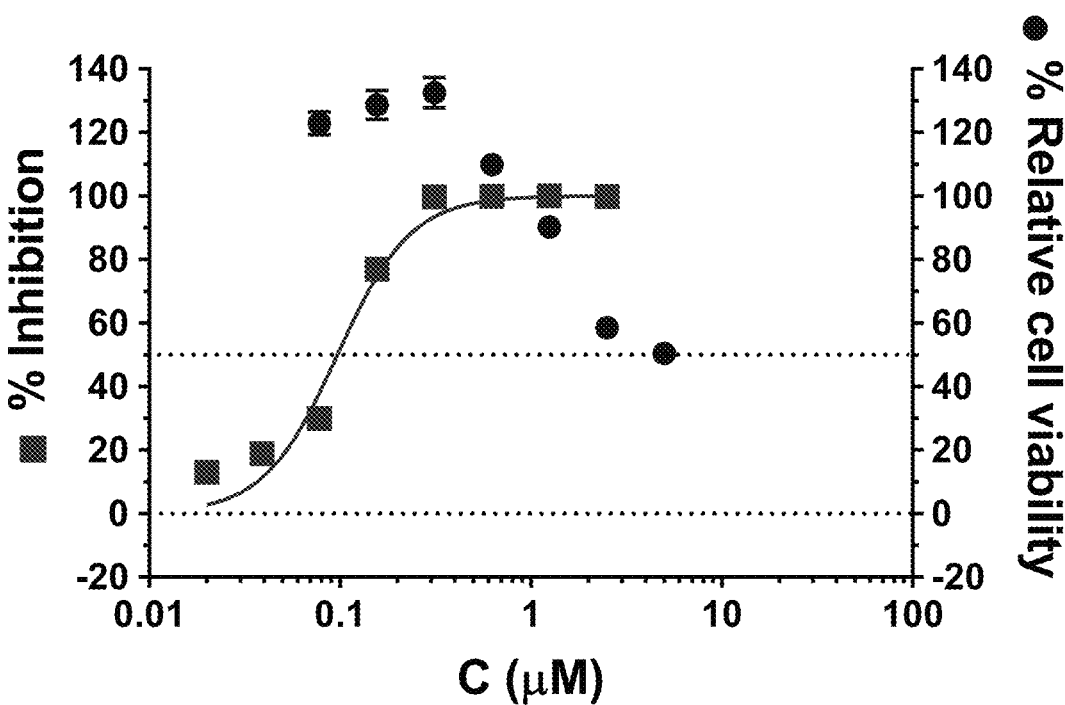
FIG. 4 shows that Compound C provided anti-SARS-CoV-2 activity, with IC50 at 97 nM and CC50 at 4.215 µM.
Figure 5:
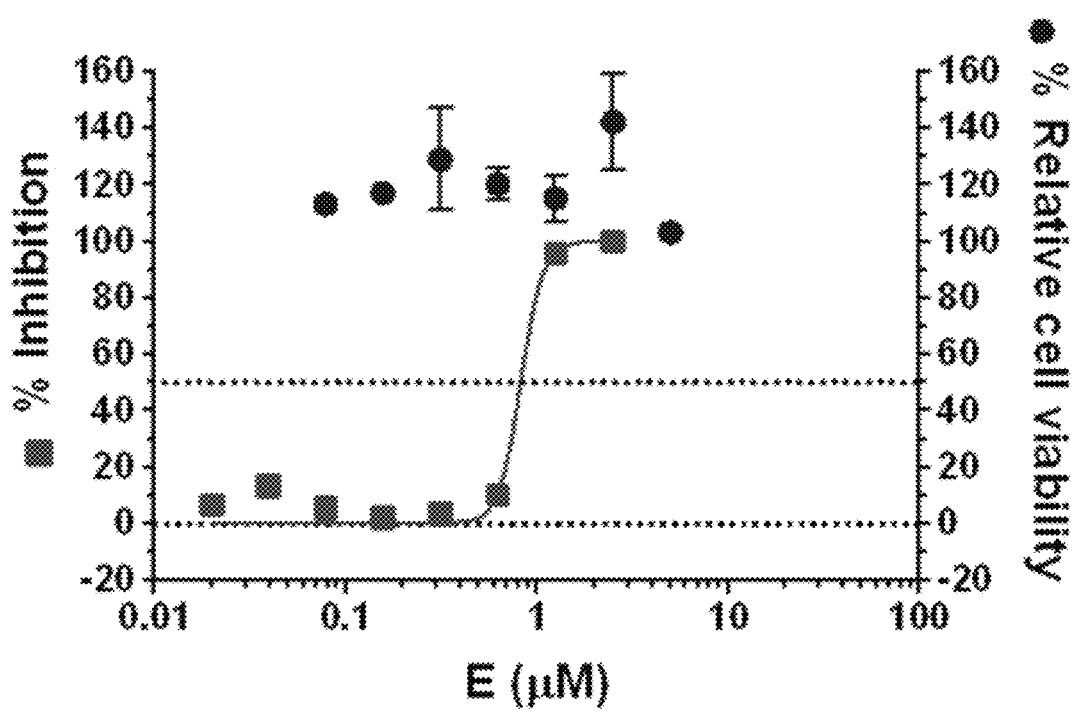
FIG. 5 shows that Compound C provided anti-SARS-CoV-2 activity, with IC50 at 0.8304 µM and CC50>5 µM.

Results:

To assess the antiviral potential of the compounds, Vero E6 cells with different concentrations of the compounds A, B, C, and E were prepared for overnight, and then the cells were infected with SARS-CoV-2 (MOI=0.01) for 2 days. The viral infection was quantified by SARS-CoV-2 N protein expression (see FIG. 1) and cytotoxicity of the compound was determined by CCK-8 assay. Among the four compounds, C (IC50 at 97 nM and CC50 at 4.215 μM, see FIG. 4) and B (IC50 at 126.3 nM and CC50 at 5.897 μM, see FIG. 3) showed good anti-SARS-CoV-2 activity, while A (IC50 at 2.743 μM and CC50>5 μM, see FIG. 2) and Control E (IC50 at 0.8304 μM and CC50>5 μM, see FIG. 5) had a lesser effect. It was concluded that Compound A, Compounds B and C reduced 75% of plaque formation at 1.25 μM.

As shown in FIGS. 2-5 providing the results of the compounds, the anti-SARS-CoV-2 activity data of each compound are listed below:

TABLE 1

Compounds used in SARS-CoV-2 plaque reduction neutralization test

| Compound | IC50 | CC50 |
| --- | --- | --- |
| Compound A | 2.743 μM | >5 μM |
| Compound B | 0.1263 μM | 5.897 μM |
| Compound C | 0.097 μM | 4.215 μM |
| Compound E | 0.8304 μM | >5 μM (21.7 μM) |

Experiment 3. Mouse Challenge Experiments.

AAV6/CB-hACE2 and AAV9/CB-hACE2 were generated by AAV Core facility of Academia Sinica. 8-10 weeks old C57BL/6 mice were anesthetized by intraperitoneal injection of a mixture of Atropine (0.4 mg/ml)/Ketamine (20 mg/ml)/Xylazine (0.4%). Mice were then intratracheally injected with $3\times10^{11}$ viral genomes (vg) of AAV6/hACE2 in 50 μL saline. To transduce extrapulmonary organs, $1\times10^{12}$ vg of AAV9/hACE2 in 100 μL saline were intraperitoneally injected into mice. After AAV6/CB-hACE2 and AAV9/CB-hACE2 transduction for 10-14 days, mice were ready for viral infection. The experimental design is listed below:

TABLE 2

Experimental design

| Group | Article | Dosage (mg/kg) | Routes | No. Animals | Sample Name |
| --- | --- | --- | --- | --- | --- |
| 1 | Solvent | NA | I.P. | 2 | AC#296-297 |
| 2 | Compound A | 50 | I.P. | 5 | AC#298-302 |

Mouse Challenged with SARS-CoV-2

AAV/hACE2 mice were anesthetized by intraperitoneal anesthesia with Zoletil 50 and intranasally challenged with $8\times10^4$ PFU of SARS-CoV-2 TCDC #4 (hCoV-19/Taiwan/4/2020 obtained from Taiwan Centers of Disease Control) (lot: IBMS20200819, 8.0E+05 PFU/ml) in a volume of 100 μL. Mouse challenge experiments were evaluated and approved by the IACUC of Academia Sinica. Surviving mice from the experiments were euthanized using carbon dioxide.

Histopathology

Figure 6:
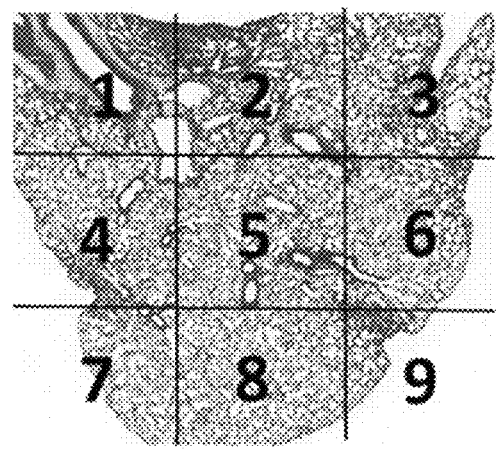
FIG. 6 shows the diagram of clinical scoring for lung histopathology.

After mouse blood samples were taken from heart, the left lung of mouse was isolated and fixed in 4% paraformaldehyde. After fixation with 4% paraformaldehyde for one week, the lung was trimmed, processed, embedded, sectioned, and stained with Hematoxylin and Eosin (H&E), followed by microscopic examination. The lung section was evaluated with a lung histopathological scoring system. The section was divided into 9 areas and numbered as shown in FIG. 6. Lung tissue of each area was scored using the scoring system in the table as shown below. The average scores of these 9 areas are used to represent the score of the animal.

TABLE 3

The scoring system of lung histopathology

| Score | Description |
| --- | --- |
| 0 | Normal, no significant finding |
| 1 | Minor inflammation with a slight thickening of alveolar septa and sparse monocyte infiltration |
| 2 | Apparent inflammation, alveolus septa thickening with more interstitial mononuclear inflammatory infiltration |
| 3 | DAD*, with alveolus septa thickening, and increased infiltration of inflammatory cells |
| 4 | DAD*, with extensive exudation and septa thickening, shrinking of alveoli, the restricted fusion of the thick septa, obvious septa hemorrhage, and more cell infiltration in alveolar cavities |
| 5 | DAD*, with massive cell filtration in alveolar cavities and alveoli shrinking, sheets of septa fusion, and hyaline membranes lining the alveolar walls |

*DAD = Diffuse alveolar damage

Statistical Analysis

Results of body weight changes, lung viral RNA titers, tissue culture infectious dose ($TCID_{50}$) from lung homogenates, and lung histopathology are presented as the bar plots with median values. For hematology CBC analysis and plasma cytokine multiplex assay, results are presented as the mean. Differences between experimental groups of animals were analyzed by one-way ANOVA, *p<0.05, p<0.01, *p<0.001.

Results

Figure 7:
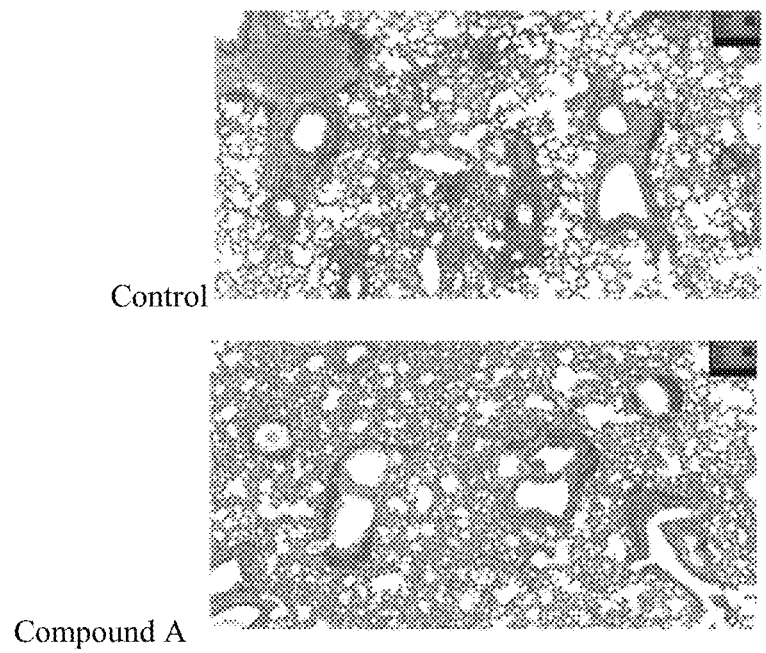
FIG. 7 shows the histopathology of the lungs in transgenic mice infected with SARS-CoV-2.
Figure 8:
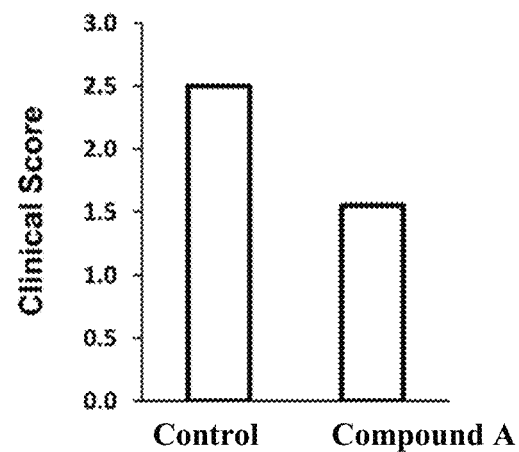
FIG. 8 shows the clinical scoring of AAV/hACE2 mice treated with solvent control and Compound A at day 5 post-SARS-CoV-2 infections.

The clinical score is shown in FIG. 7 and FIG. 8. The results showed that 50 mg/kg of Compound A-treated mice exhibited a significant difference reduced clinical score of lung histopathology to less than 2 (2 out of 5).

It is expressly predicted from the results that by inhibiting virus through a multiple mode of actions, the compounds should be able to develop a broad spectrum antiviral drug to treat other RNA viruses, such as HCV and HDV.

In conclusion, each of Compound A, Compound B or Compound C had good anti-viral performance. It is also suggested that these compounds are potent to develop broad spectrum anti-viral drugs.

All publications, patents, and patent documents cited herein above are incorporated by reference herein, as though individually incorporated by reference.

The invention has been described with reference to various specific and preferred embodiments and techniques. However, one skilled in the art will understand that many variations and modifications may be made while remaining within the spirit and scope of the invention.

What is claimed is:

1. A method for treating an RNA viral infection in a human comprising administering a therapeutically effective amount of:

Compound A

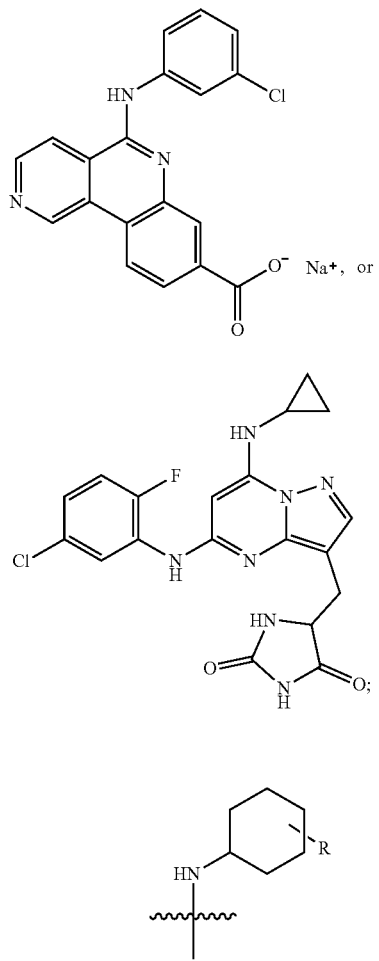

or a pharmaceutically acceptable salt thereof.

2. The method of claim 1 comprising administering a therapeutically effective amount of Compound A

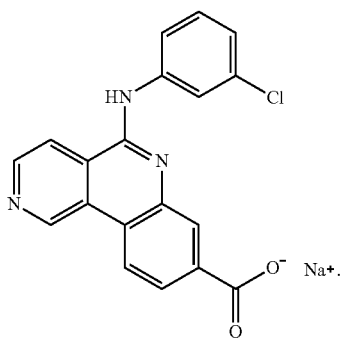

3. The method of claim 2, wherein the RNA virus is severe acute respiratory syndrome-related coronavirus (SARS-CoV), or SARS-CoV-2.

4. The method of claim 3, wherein the RNA viral infection is COVID-19.

5. The method of claim 1, wherein the RNA virus is severe acute respiratory syndrome-related coronavirus (SARS-CoV), or SARS-CoV-2.

6. The method of claim 1, wherein the RNA viral infection is COVID-19.

* * * * *

UNITED STATES PATENT AND TRADEMARK OFFICE
CERTIFICATE OF CORRECTION

Page 1 of 2

PATENT NO. : 11,696,911 B2
APPLICATION NO. : 17/205823
DATED : July 11, 2023
INVENTOR(S) : Tai-Sen Soong It is certified that error appears in the above-identified patent and that said Letters Patent is hereby corrected as shown below:

In the Claims

Column 33, beginning on Line 16, in Claim 1:
Change:

"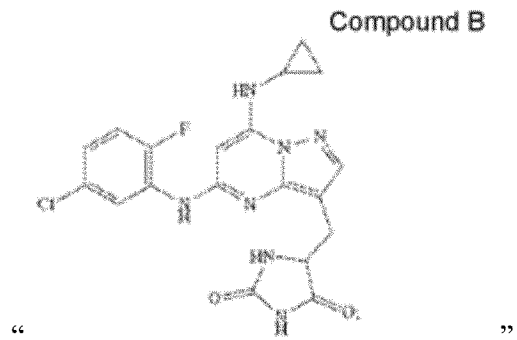"

To:

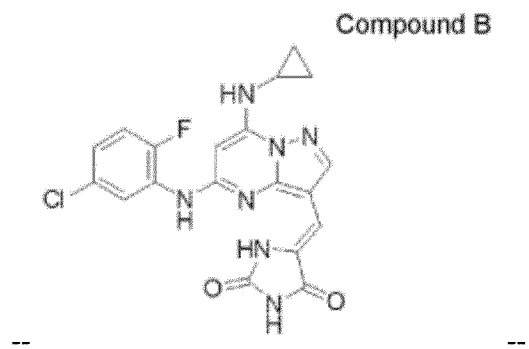

--

Signed and Sealed this
Fifth Day of December, 2023

Katherine Kelly Vidal
*Director of the United States Patent and Trademark Office*

Column 33, beginning on Line 31, in Claim 1:
Change:
" 
or a pharmaceutically acceptable salt thereof."
To:
--or a pharmaceutically acceptable salt thereof.--